United States Patent
Binder et al.

(10) Patent No.: US 7,667,061 B2
(45) Date of Patent: Feb. 23, 2010

(54) METHOD OF PREPARING A COMPOSITION USING ARGENTATION CHROMATOGRAPHY

(75) Inventors: Thomas P. Binder, Decatur, IL (US); Doug Geier, Decatur, IL (US); Ahmad K. Hilaly, Forsyth, IL (US); Robert Duane Sandage, Decatur, IL (US); John G. Soper, Mt. Zion, IL (US)

(73) Assignee: Archer-Daniels-Midland Company, Decatur, IL (US)

(*) Notice: Subject to any disclaimer, the term of this patent is extended or adjusted under 35 U.S.C. 154(b) by 374 days.

(21) Appl. No.: 11/612,250

(22) Filed: Dec. 18, 2006

(65) Prior Publication Data

US 2007/0181504 A1  Aug. 9, 2007

Related U.S. Application Data

(60) Provisional application No. 60/750,794, filed on Dec. 16, 2005.

(51) Int. Cl.
*C11B 7/00* (2006.01)
*B01D 15/00* (2006.01)

(52) U.S. Cl. .................. 554/194; 554/193; 210/667; 210/656

(58) Field of Classification Search .............. 554/175, 554/191, 193, 194; 210/656, 667
See application file for complete search history.

(56) References Cited

U.S. PATENT DOCUMENTS

| | | | |
|---|---|---|---|
| 2,985,589 A | 5/1961 | Broughton et al. | |
| 4,049,688 A | 9/1977 | Neuzil et al. | |
| 4,277,413 A | 7/1981 | Logan | |
| 4,282,164 A | 8/1981 | Logan et al. | |
| 4,297,292 A * | 10/1981 | Logan et al. | 554/187 |
| 4,305,882 A | 12/1981 | Emken et al. | |
| 4,480,108 A | 10/1984 | Foster | |
| 4,529,828 A | 7/1985 | Antos et al. | |

(Continued)

FOREIGN PATENT DOCUMENTS

EP    0 062 113 A1    10/1982

(Continued)

OTHER PUBLICATIONS

Kirk-Othmer, Encyclopedia of Chemical Technology, Fourth Edition, 1993, vol. 10, (3 pages).*

(Continued)

*Primary Examiner*—Rosalynd Keys
*Assistant Examiner*—Yate' K Cutliff
(74) *Attorney, Agent, or Firm*—Sterne, Kessler, Goldstein & Fox P.L.L.C.

(57) ABSTRACT

The present invention is directed to a method of preparing compositions enriched in compounds containing carbon chains of varying degrees of unsaturation using argentation chromatography. The present method utilizes an argentized cationic resin or a conditioned argentized alumina to separate compounds containing saturated or mono-unsaturated carbon chains from compounds having polyunsaturated carbon chains present in a starting composition. The invention is particularly useful for preparing a composition enriched in polyunsaturated fatty acid alkyl esters from mixtures of fatty acid esters in a starting composition derived from vegetable oils. The present invention is also directed to a method of preparing a conditioned argentized alumina adsorbent having increased selectivity for compounds containing one or more polyunsaturated carbon chains.

18 Claims, 10 Drawing Sheets

U.S. PATENT DOCUMENTS

| | | | |
|---|---|---|---|
| 4,961,881 | A | 10/1990 | Ou |
| 5,117,016 | A | 5/1992 | Tackett et al. |
| 5,424,457 | A | 6/1995 | Sumner, Jr. et al. |
| 5,504,220 | A | 4/1996 | Kuo et al. |
| 5,672,726 | A | 9/1997 | Ryu et al. |
| 5,786,491 | A | 7/1998 | Hamlin et al. |
| 6,153,774 | A | 11/2000 | Seidel |
| 6,410,763 | B1 | 6/2002 | Seidel |
| 6,673,945 | B2 | 1/2004 | Binder et al. |
| 6,706,898 | B2 | 3/2004 | Sumner, Jr. |
| 6,867,308 | B2 | 3/2005 | Bartok et al. |

FOREIGN PATENT DOCUMENTS

| | | |
|---|---|---|
| EP | 1 106 602 A1 | 6/2001 |
| WO | WO 00/71546 A1 | 11/2000 |
| WO | WO 2006/116419 A1 | 11/2006 |

OTHER PUBLICATIONS

Aerojet Fine Chemicals, "Simulated Moving Bed Chromatography," accessed online at http://www.aerojetfinechemicals.com/smbtheory.html, Aerojet Fine Chemicals, 21 pages (accessed Aug. 2004).

Albany Molecular Research, "Simulated Moving Bed Chromatography," *Technical Reports 4*:1-2, Albany Molecular Research, Inc. (2000).

Bertucco, A., and Sanmartin, F., "Simulated Moving Bed Technology for Continuous, Countercurrent Solid-Fluid Supercritical Extraction," *J. Supercritical Fluids 8*:138-148, PRA Press (1995).

Breuer, B., et al., "Separation of Fatty Acids or Methyl Esters Including Positional and Geometric Isomers by Alumina Argentation Thin-Layer Chromatography," *J. Chromatogr. Sci. 25*:302-306, Preston Technical Abstracts (1987).

Cert, A., and Moreda, W., "New method of stationary phase preparation for silver ion column chromatography: Application to the isolation of steroidal hydrocarbons in vegetable oils," *J. Chromatogr. A 823*:291-297, Elsevier Science B.V. (1998).

Chapman, L.R., and Kuemmel, D.F., "Liquid-Solid and Capillary Gas-Liquid Chromatography of Internal Olefin Isomers," *Anal. Chem. 37*:1598-1600, American Chemical Society (1965).

De Vries, B., "Quantitative Separations of Higher Fatty Acid Methyl Esters by Adsorption Chromatography on Silica Impregnated with Silver Nitrate," *J. Amer. Oil Chem. Soc. 40*:184-186, American Oil Chemists' Society (1963).

Dejarlais, W.J., et al., "Acetonitrile as Eluent in Silver Resin Column Chromatography," *J. Amer. Oil Chem. Soc. 60*:975-978, American Oil Chemists' Society (1983).

Juza, M., "Development of a high-performance liquid chromatographic simulated moving bed separation from an industrial perspective," *J. Chromatogr. A 865*:35-49, Elsevier Science B.V. (1999).

Momchilova, S., and Nikolova-Damyanova, B., "Stationary phases for silver-ion chromatography of lipids: Preparation and properties," *J Sep. Sci. 26*:261-270, Wiley-VCH Verlag GmbH & Co. (2003).

Nikolova-Damyanova, B., "Lipid analysis by silver-ion chromatography," in *Advances in Lipid Methodology—Five*, Adlof, R.O., et al., eds., Oily Press Library, Bridgwater, UK, pp. 43-123, (2003).

Organo Corporation, "Simulated Moving-Bed Chromatography," accessed online at http://www.organo.co.jp/technology/hisepa/en_hisepa/chromato/c5.html, Organo Corporation, 3 pages (accessed Aug. 2004).

Scholfield, C.R., "Argentation High Performance Liquid Chromatography on Methyl Esters," *J. Amer. Oil Chem. Soc. 57*:331-334, American Oil Chemists' Society (1980).

Scholfield, C.R., and Mounts, T.L., "New Developments in Silver Resin Chromatography of *cis* and *trans* Fatty Methyl Esters," *J. Amer. Oil Chem. Soc. 54*:319-321, American Oil Chemists' Society (1977).

Zinkel, D.F., and Rowe, J.W., "Thin-Layer Chromatograpy of Resin Acid Methyl Esters," *J. Chromatogr. 13*:74-77, Elsevier Science B.V. (1964).

Morris, L.J., "Separations of lipids by silver ion chromatography," *J. Lipid Res. 7*:717-732, Federation of American Societies for Experimental Biology (1966).

Emken, E.A., et al., "Separation of Saturated, Unsaturated, and Acetylenic Fatty Acid Isomers by Silver Resin Chromatography," *Journal of the American Oil Chemists' Society 55*:561-563, American Oil Chemists Society (1978).

Sikavitsas, V.I., et al., "Magnetically Stabilized Fluidized Bed for Gas Separations: Olefin-Paraffin Separations by $\pi$-Complexation," *Ind. Eng. Chem. Res. 34*:2873-2880, American Chemical Society (1995).

\* cited by examiner

METHOD OF PREPARING A COMPOSITION USING ARGENTATION CHROMATOGRAPHY

CROSS REFERENCE TO RELATED APPLICATIONS

This application claims the benefit of U.S. Provisional Application No. 60/750,794, filed Dec. 16, 2005, which is incorporated by reference herein in its entirety.

BACKGROUND OF THE INVENTION

1. Field of the Invention

The present invention is related to methods of preparing compositions enriched in compounds containing carbon chains having various degrees of saturation. The present method is related to simulated moving bed chromatography using an argentized adsorbent.

2. Background of the Invention

The use of silver ion chromatography for separation of fatty acid methyl esters (FAME) by the degree of unsaturation of the fatty acid moiety is known (Nikolova-Damyanova, B., *Advances in Lipid Methodology-Five:*43-123, Oily Press Library (2003)). Silver ion thin-layer chromatography (TLC) and batch column chromatography of FAME uses silver-treated silicic acid, silica gel or ion-exchange resin as a support (Nikolova-Damyanova, B., *Advances in Lipid Methodology-Five:*43-123, Oily Press Library (2003)). Alumina has been used without silver ion for separation of paraffins from olefins (U.S. Pat. No. 2,985,589); however, aluminosilicates were the preferred supports. Argentized (silver-ion treated) neutral alumina has also been used to separate cis from trans octadecene olefins (Chapman, L. and Kuemmel, D., *Anal. Chem.* 37:1598-1600 (1965)). For separation of FAME by TLC, argentized alumina has been used to separate methyl stearate, methyl oleate, and methyl linoleate (Zinkel, D. and Rowe, J., *J. Chromatogr.* 13:74-77 (1964)); later, these were also separated from methyl linolenate, trans configurations, and methyl esters of longer-chain fatty acids (Breuer, B. et al., *J. Chromatogr. Sci.* 25:302-306 (1987)). However, these analytical separations are carried out discontinuously (batch-wise) and are not amenable to use in large scale to produce commercially useful quantities of composition enriched in carbon compounds having a desired degree of unsaturation.

Liquid chromatography (LC) separation of FAME on silica-based supports such as silica gel (U.S. Pat. No. 5,672,726) and silicic acid (de Vries, B., *J. Amer. Oil Chem. Soc.* 40:184-186 (1963)) has been reported. Argentized macroreticular ion-exchange resin, such as Amberlite XE-284 (Scholfield, C., *J. Amer. Oil Chem. Soc.* 57:332-334 (1980); Scholfield, C. and Mounts, T., *J. Amer. Oil Chem. Soc.* 54:319-321 (1977); DeJarlais, W., et al., *J. Amer. Oil Chem. Soc.* 60:975-978 (1983)), and argentized ion exchange resins with strong sulfonic acid groups (U.S. Pat. Nos. 4,305,882; 6,153,774; and 6,410,763) have also been used for LC separation of FAME on the basis of unsaturation and double bond isomers (cis or trans). The use of alumina as a support for separation of FAME has been advised against because it reacts with some lipids and solvents (Monchilova, S. and Nikolova-Damyanova, B., *J. Sep. Sci.* 26:261-270 (2004)). Silica gel is the most widely used support for LC separation of FAME (Cert, A. and Moreda, W., *J. Chromatog. A* 823:291-297 (1998)). However, these batch processes operate discontinuously, rendering them unattractive for large-scale separation of compounds based on desired degree of unsaturation.

It is widely taught that great care is needed in the preparation of argentized supports for the separation of lipids (Nikolova-Damyanova, B., *Advances in Lipid Methodology-Five:*43-123, Oily Press Library (2003); Breuer, B., et al., *J. Chromatogr. Sci.* 25:302-306 (1987)). Difficulties cited include the lack of robustness and homogeneity in available support materials, (Cert, A. and Moreda, W., *J. Chromatog.* A823:291-297 (1998)) and inherent instability due to sensitivity to light and moisture (Monchilova, S. and Nikolova-Damyanova, B., *J. Sep. Sci.* 26:261-270 (2004)). Recommended precautions include protecting argentized supports from exposure to light by packing into stainless steel columns (DeJarlais, W., et al., *J. Amer. Oil Chem. Soc.* 60: 975-978 (1983)) or wrapping with a dark cloth (de Vries, B., *J. Amer. Oil Chem. Soc.* 40:184-186 (1963); U.S. Pat. Nos. 6,153,774 and 6,410,763). This precaution is not limited to argentized silica; heat activation treatment of argentized alumina TLC plates was limited to 15 minutes and 70° C. to prevent darkening of the adsorbent (Breuer, B., et al., *J. Chromatogr. Sci.* 25:302-306 (1987)).

Although simulated moving bed (SMB) chromatography has been used for many years in the separation of sugars and petrochemicals (Juza, M., *J. Chromatog.* A865:35-49 (1999)), it has had limited application in separation of oily substances. SMB has been used with supercritical $CO_2$ to extract oilseeds and separate alpha-tocopherol from oleic acid (Bertucco, A., et al., *J. Supercritical Fluids* 8:138-148 (1995)). A solid bed technique employing zeolites exchanged with potassium has been applied to separation of methyl oleate and methyl linoleate from methyl stearate and methyl palmitate; however, no silver ion is used in the process (U.S. Pat. No. 4,049,688).

SUMMARY OF THE INVENTION

The present invention is directed to a method of preparing compositions enriched in compounds containing carbon chains having desired degrees of unsaturation by simulated moving bed chromatography using an argentized adsorbent. The present method utilizes an argentized cationic resin or a conditioned argentized alumina in a simulated moving bed chromatography process to separate compounds containing saturated carbon chains from compounds containing unsaturated carbon chains present in a starting composition.

In addition, the present process can be used to separate saturated and/or monounsaturated carbon chains from compounds having polyunsaturated carbon chains present in a starting composition.

In addition, the present process can be used to separate saturated carbon chains, monounsaturated carbon chains, and polyunsaturated carbon chains present in a starting composition into three fractions, each fraction being enriched in carbon chains having differing degrees of unsaturation.

In addition, the present process can be used to separate saturated carbon chains, monounsaturated carbon chains, diunsaturated carbon chains and triunsaturated carbon chains present in a starting composition into four fractions, each fraction being enriched in carbon chains having differing degrees of unsaturation.

The invention is particularly useful for preparing a composition enriched in monounsaturated and polyunsaturated fatty acid alkyl esters from mixtures of fatty acid esters in a starting composition derived from vegetable oils. The present invention is also directed to a method of preparing a conditioned argentized alumina adsorbent having a darker color than non-aged adsorbent and/or increased selectivity for compounds containing one or more unsaturated carbon chains.

DETAILED DESCRIPTION OF THE INVENTION

Figure 1:
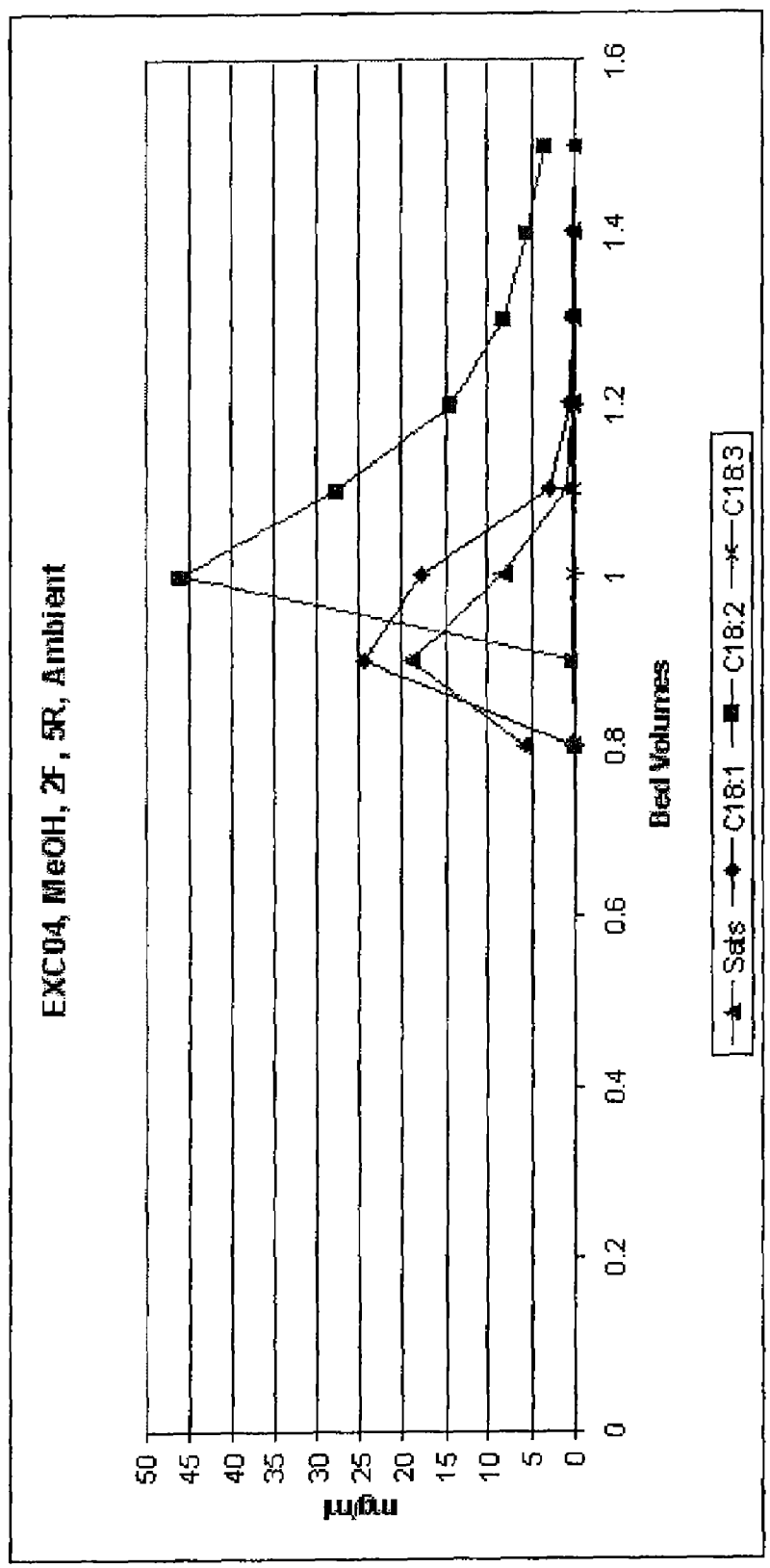
FIG. 1 depicts an elution profile of a pulse test for the separation of soy fatty acid methyl esters on argentized cationic EXC04 resin from Example 1 eluted with methanol and effluents enriched in FAME of varying degrees of unsaturation are collected.

The present invention includes methods of preparing a composition enriched in compounds containing unsaturated carbon chains by simulated moving bed chromatography using an argentized adsorbent.

In one embodiment of the present method, compounds containing at least one unsaturated carbon chain in a first composition can be separated from the first composition to form a composition enriched in compounds containing at least one unsaturated carbon chain.

In another embodiment of the present method, a composition can be separated into at least two fractions based on degree of unsaturation wherein, at least one of the fractions is enriched in compounds containing at least one saturated carbon chain and/or mono-unsaturated carbon chain, and at least one of the fractions is enriched in compounds containing at least one polyunsaturated carbon chain. Alternatively, at least one fraction is enriched in compounds containing at least one saturated carbon chain and at least one fraction is enriched in compounds containing at least one monounsaturated carbon chain and/or one polyunsaturated carbon chain. This preferred method comprises:

(a) combining a first composition comprising, i) at least one compound containing at least one saturated or mono-unsaturated carbon chain, and ii) at least one compound containing at least one saturated or polyunsaturated carbon chain, with an argentized adsorbent selected from the group consisting of a cationic resin and a conditioned alumina, wherein the adsorbent, at the time of use is contained on chromatographic beds, columns or parts thereof, wherein the alumina, prior to combining with the first composition has been subjected to a conditioning process for at least about 24 hours in the absence of the first composition, the alumina having a Hunter L color value that is at least about 10% lower than the color value prior to conditioning;

(b) contacting the combined first composition and the adsorbent with one or more solvent(s) simultaneously or in sequence; and (c) separating at least a second composition that is enriched relative to the first composition in at least one of the compounds containing at least one saturated, monounsaturated, or polyunsaturated carbon chain, wherein a composition enriched in one or more of the saturated, monounsaturated or polyunsaturated compounds is prepared and passed out of a simulated moving bed apparatus as an effluent.

A composition that is enriched in a compound or compounds has a higher concentration of the compound or compounds relative to the starting composition. A composition can also be enriched with regard to the relative concentration of each polyunsaturated compound, whereby the concentration of one or more polyunsaturated compounds can increase relative to any other polyunsaturated compounds relative to the concentrations in the starting composition.

In another embodiment, the first composition of step a) contains at least one saturated carbon chain, at least one monounsaturated carbon chain, and at least one polyunsaturated carbon chain. After steps a) and b) are executed, step c) may be carried out to separate at least one second composition that is enriched relative to the first composition in at least one of the compounds containing at least one saturated, monounsaturated, or polyunsaturated carbon chain, wherein a composition enriched in one or more of the saturated, monounsaturated or polyunsaturated compounds is prepared.

In another embodiment, a second and a third composition are recovered, wherein one of the second and third compositions is enriched in saturated and monounsaturated carbon chains, and one is enriched in polyunsaturated carbon chains.

In another embodiment, a second, third and fourth composition are recovered, wherein one of the second, third and fourth compositions is enriched in saturated carbon chains, another is enriched in monounsaturated carbon chains, and another is enriched in polyunsaturated carbon chains.

In another embodiment, a second, third, fourth and fifth composition are recovered, wherein one of the second, third, fourth and fifth compositions is enriched in saturated carbon chains, another is enriched in monounsaturated carbon chains, and another is enriched in polyunsaturated carbon chains, and another is enriched in polyunsaturated carbon chains having a different degree of unsaturation than the other fraction enriched in polyunsaturated carbon chains.

"Degree of unsaturation" is also described as "degree of saturation", and indicates the number of double bonds in a carbon chain, and may be 0, 1, 2, 3, 4, 5 or 6.

Useful adsorbents include argentized resin or alumina. If the adsorbent is a resin, then the resin will have been argentized as described herein to form the useful adsorbent. Resins suitable for argentation include resins capable of complexing with a silver ion. These include cationic resins, such as, strong acid ion exchange resins including but not limited to strong acid cation exchange resin containing sulfonic acid moieties. If the adsorbent is a conditioned argentized alumina, the alumina will have been argentized and conditioned as described herein to form the useful adsorbent. Preferably, the alumina is spherical. Also preferred is alumina having a surface area of from about 100 to about 400 square meters/gram, more preferably from about 150 to about 350, and most preferably about 150.

The present method prepares a composition enriched in compounds containing at least one unsaturated carbon chain by separating the components of a first composition. The first composition, therefore, will comprise a mixture of components. In one embodiment, the first composition comprises a mixture such that at least one compound contains a polyunsaturated carbon chain, and at least one compound contains a saturated carbon chain or a monounsaturated carbon chain. In another embodiment, the first composition will comprise a mixture of components such that at least one compound contains a polyunsaturated carbon chain and at least one compound contains a monounsaturated carbon chain. In yet another embodiment, the first composition will comprise a mixture of components such that at least one compound contains a polyunsaturated carbon chain, at least one compound contains a monounsaturated carbon chain, and at least one compound contains a saturated carbon chain. In still yet another embodiment, the first composition will comprise a mixture of components such that at least one compound contains a monounsaturated carbon chain, and at least one compound contains a saturated carbon chain.

As used herein, a carbon chain can be anywhere from about 3 to about 80 carbons in length. Preferably, the carbon chain is from about 10 to about 30 carbons in length. The most preferred carbon chains are from about 12 to about 24 carbons in length. The chains can be identified by referring to the number of carbon atoms in the acyl moiety of the carbon chain, the number of double bonds and, if necessary to identify, the location of the double bonds. Thus, C18:1 (or 18:1) refers to a carbon chain having an acyl moiety 18 carbons in length and having one double bond. The compounds that contain the carbon chain will also contain other moieties unless the unsaturated carbon chain is an unsubstituted olefin hydrocarbon. When present, the other moieties can be esters, hydroxyls, polyols, epoxides, amines, amides, aryls, heteroaryls, thiols and the like.

A preferred first composition is derived from oils or fats and will contain an ester linkage that binds to the carbon chain, which is a fatty acid alkyl chain. Such ester linkages can comprise a monoester compound or can be a linkage that connects the carbon chain to a polyol or a polyester, such as a di- or triglyceride.

Preferably, the first composition is derived from oils, fats and waxes (collectively known as lipids). The first composition will therefore contain a variety of fatty acid alkyl chains that are characteristic of the lipid. These lipids include wood oils such as tung oils; animal-derived oils, such as tallow, lard, poultry grease, or lanolin; and vegetable oils. Preferred vegetable oils include, but are not limited to, soybean oil, linseed oil, sunflower oil, castor oil, corn oil, canola oil, rapeseed oil, palm kernel oil, cottonseed oil, peanut oil, coconut oil, palm oil, tung oil, safflower oil and derivatives, conjugated derivatives, genetically-modified derivatives and mixtures thereof. As used herein, a reference to a vegetable oil includes all its derivatives such as fatty acids, fatty acid alkyl esters and mono- or di-glycerides. Conjugated fatty acids, such as those formed by hydrogenation, deodorization, heat-treatment, or blowing of polyunsaturated oils or fatty acids are suitable feedstocks.

More preferably, the first composition is derived from vegetable oils and comprises fatty acid ($C_{1-5}$) alkyl esters. The preparation of fatty acid ($C_{1-5}$) alkyl esters from fats and oils, and particularly, vegetable oils is well-known in the art. These fatty acid alkyl esters include, but are not limited to, esters of saturated fatty acids, including but not limited to lauric acid, myristic acid, palmitic acid, stearic acid, or arachidic acid; esters of monounsaturated acids, including, but not limited to palmitoleic acid, oleic acid, erucic acid, or elaidic acid; and esters of polyunsaturated fatty acids, including but not limited to linoleic acid, linolenic acid, eleostearic acid, ricinoleic acid, arachidonic acid, cetoleic acid, eicosapentaenoic acid, or docosahexaenoic acid. Esters of polyunsaturated fatty acids may contain 2, 3, 4, 5, 6 or more double bonds in the acyl moiety of the carbon chain. More preferred alkyl esters include fatty acid ethyl and methyl esters (FAME).

In certain embodiments, the present method utilizes a conditioned argentized alumina adsorbent. The alumina can be acidic or neutral depending on the treatment it is given during preparation as described herein. The conditioning of the adsorbent can be performed before or after loading the adsorbent on chromatographic beds, columns or parts thereof.

Prior to conditioning, an argentized alumina will have an initial selectivity when argentized. A conditioned argentized alumina means that the alumina is not used at the time of argentation. Rather, it is subjected to conditioning for at least about 24 hours, or more preferably 48 hours, and most preferably 72 hours. The conditioning process improves the selectivity of argentized alumina to compounds based on degree of unsaturation of the acyl moiety of the carbon chain and/or causes the argentized alumina to darken in color. The selectivity is calculated by the following equation:

$$\text{Coefficient of selectivity} = (B) = \frac{[vol.percentC / vol.percentD]_A}{[vol.percentC / vol.percentD]_U} \quad \text{Equation I}$$

Where: $A$ = adsorbed phase
$U$ = unadsorbed phase
$C$ = first component(s)
$D$ = second component(s)

Thus, the coefficient of selectivity (B) (also referred to herein as "selectivity") of an adsorbent is the ratio of the first component and second component in the adsorbed phase, divided by the ratio of the first component and second component in the unadsorbed phase when measured.

In one embodiment, the first component comprises saturated FAME and the second component comprises unsaturated FAME. In another embodiment, the first component comprises saturated FAME and monounsaturated FAME and the second component comprises polyunsaturated FAME.

The conditioning process described herein can increase the selectivity (B) and can be determined by comparing the initial selectivity, designated $B_1$ with a post-conditioning, second selectivity, $B_2$. The selectivity (B) for an alumina can be determined by sampling a portion of the alumina before and after conditioning and contacting each with a composition comprising at least a first component comprising a first degree of unsaturation and a second component comprising a second, different, degree of unsaturation. Such contact can be carried out by running a pulse test on a single column, which does not require a simulated moving bed process. The values of the denominator of equation 1 can be obtained by determining the contents of C and D in liquid phase after contact with the adsorbent. The values of the numerator of equation 1 ([vol.percentC/vol.percentD]$_A$) can be obtained by removing adsorbent from contact with the unadsorbed phase, eluting the adsorbed phase from the adsorbent and causing it to pass out of the column as an effluent, and determining the contents of C and D from the adsorbed phase.

Selectivity can also be conveniently expressed as the denominator of equation 1 ([vol.percentC/vol.percentD]$_U$), as the ratio of C to D in the unadsorbed phase. The content of C and D in the unadsorbed phase can be easily determined by subjecting the unadsorbed phase to analysis, such as by gas-liquid chromatography. In some embodiments herein in which saturated methyl esters are separated from unsaturated (monounsaturated plus polyunsaturated) methyl esters, the ratio of C to D in the unadsorbed phase is expressed as saturated methyl esters to unsaturated methyl esters (SME/UME).

As the coefficient of selectivity (B) is a quotient, values close to one represent approximately equal amounts of C and D in the unadsorbed and adsorbed phases, and thus poor selectivity. As selectivity increases, values farther from one are obtained. As the coefficient of selectivity (B) approaches 1.000, there is a decrease in the preferred selectivity of one component, by the adsorbent, over the other. As B becomes less than 1.000, there is a preferred adsorption of component D such that the effluent of the column is enriched in component C. As B becomes greater than 1.000, there is a preferred adsorption of component C such that the column effluent is enriched in component D.

Calculations are based on weight percent of the components. Thus, greater differences from 1.000 in B values or in the saturate/unsaturate (e.g., SME/UME) ratio indicate a better selectivity between saturated and unsaturated carbon chain containing compounds.

What is meant by eluting is the interaction between an adsorbed phase and a solvent, in which a portion of the adsorbed phase selectively desorbs from the adsorbed phase in the presence of the solvent. An adsorbed phase is prepared by loading a mixture of two or more carbon compounds having varying degrees of separation (such as, at least one compound containing at least one saturated carbon chain, and at least one compound containing at least one unsaturated carbon chain) onto an argentized adsorbent. Subsequently, solvents are applied to selectively elute (desorb) compounds of the desired degree of unsaturation.

In the present disclosure, portions of the adsorbed phase are desorbed based on the number of double bonds (the degree of unsaturation) of the components of the feed or adsorbed phase. The solvent becomes enriched in compound containing at least one carbon chain of a given degree of unsaturation, and the adsorbed phase becomes depleted in that at least one carbon chain of that same degree of unsaturation. This elution typically takes place in a zone; the eluted material can then be caused to pass out of the SMB as an effluent enriched in at least one carbon chain of that degree of unsaturation, and the adsorbent bed can be caused to pass into the next zone for further treatment.

It has been found that selectivity (B) and SME/UME increase when the argentized alumina is subjected to a conditioning process, which comprises exposure to solvent. The initial selectivity ($B_1$) of the argentized alumina is the selectivity prior to 24 hours of exposure to solvent or prior to combining with the composition to be enriched. The conditioned selectivity ($B_2$) is the selectivity after 24 hours of exposure to solvent, or after combining with the composition to be enriched. In all embodiments, the aged argentized alumina will have a $B_1$ value between 1.000 and the value of $B_2$. An efficient way of determining the $B_1$ and $B_2$ values is by the sampling method described above.

It has also been found that selectivity (B) can relate to the color value of the argentized alumina expressed as the Hunter L color. An argentized alumina that has been subjected to conditioning conditions will possess a Hunter L color value (or any other appropriate color determination) that is at least about 10% darker (about a 10% lower Hunter L color value) than the argentized alumina at the time of manufacture. The conditioned argentized alumina has a Hunter L color value that is at least about 20% lower than the Hunter L color value of the alumina prior to conditioning. Preferably, the color value is at least about 25% darker (about a 25% lower Hunter L color value), and most preferably about 50% lower (about a 50% lower Hunter L color value). An absolute color value for the aged argentized alumina is below about 70. More preferably, the color value is below about 50. Most preferably, the color value is below about 35.

The present invention is directed to a method of preparing a conditioned argentized alumina adsorbent, comprising:

(a) providing an argentized alumina adsorbent having: i) an initial selectivity ($B_1$) as determined by the equation I above; and ii) an initial Hunter L color value (IHC);

(b) subjecting the argentized alumina to a conditioning process whereby a conditioned argentized alumina absorbent having: i) a selectivity ($B_2$) as determined by the equation I above; and, ii) a Hunter L color value (HC-2);

wherein, $B_1$ is a value between $B_2$ and 1.000, and HC-2 is at least about 10% lower than IHC; wherein a conditioned argentized alumina adsorbent is prepared.

The conditioning process can comprise contacting the alumina with a liquid for a portion or all of the conditioning. The liquid is preferably a weakly polar to non-polar solvent, such as straight chain or branched hydrocarbons including but not limited to pentanes, hexanes, heptanes, octanes, nonanes, decanes, petroleum ethers; and weakly polar esters, such as ethyl acetate. Preferably, the adsorbent is contacted with a solvent for essentially the entire conditioning process time, but this is not a requirement as contacting the adsorbent with a solvent for a portion of the time can be sufficient to yield a conditioned adsorbent having the desired properties as described herein.

The adsorbent may be contacted with a solvent in a batch mode to yield a conditioned adsorbent and loaded into columns for use in separation. In another embodiment, the adsorbent may be loaded into columns and contacted with a solvent to yield a conditioned adsorbent.

The elution solvent(s) used in the simulated moving bed chromatographic process can be any solvent useful for solvating compounds having at least one carbon chain. Such solvents include solvents capable of solvating lipids, such as organic solvents that include ethyl acetate, aliphatic compounds, aromatic compounds, and alcohols. In one embodiment employing argentized ion exchange resins in a simulated moving bed configuration, preferably, the solvents are alcohols, such as C1-5 alkyl alcohols. More preferred solvents include isopropanol, ethanol and methanol.

In one embodiment employing conditioned alumina in a simulated moving bed configuration, useful solvents are non-polar solvents such as ethyl acetate, hexane, heptane, and other aliphatic or aromatic non-polar solvents. Polar solvents are often incompatible with alumina, leading to deterioration of the physical alumina matrix.

When more than one solvent is used, the solvents can be used simultaneously, such that different zones of the adsorbent and the desired compounds are in contact with different solvents at the same time. Also, the solvents can be used in sequence such that the adsorbent in a given zone and the desired compounds are contacted with predominately one or the other solvent.

As Simulated Moving Bed is carried out in a continuous manner, simultaneous application of solvents in different parts of the SMB apparatus is preferred. The Simulated Moving Bed (SMB) is divided into zones, wherein each zone may be distinguished from the other zones by the solvent flow applied to the SMB in that zone. Zones may also be distinguished by the effluent flowing from them. In an embodiment, two solvents can be applied in a gradient fashion, so that the solvent applied is enriched in a first solvent; a gradient increasing in content of a second solvent may be applied so that the relative content of first solvent decreases and the relative content of the second solvent increases. For example, compounds comprising saturated carbon chains are caused to pass out of the SMB as effluents in the zone closest to the loading zone, and adsorbent enriched in unsaturated compounds passes into the next zone of the SMB.

In pulse tests carried out on single columns with two solvents, employing sequential application of solvents and thus step-wise elution, separate values for selectivity coefficients are obtained for each solvent. For example, the 0-2 BV (Bed Volume) Selectivity coefficients may define the selectivity coefficient of a first eluent while the 2-4 BV Selectivity coefficients may define the selectivity coefficient of a second eluant.

A single-column discontinuous preliminary test used in the art of simulated moving bed chromatography to identify suitable chromatographic conditions for purification of desired compounds may be carried out. One suitable name for such a test is a "Pulse Test". A pulse test can be carried out by preparing an adsorbent material in a single column.

If necessary, a conditioning step can be applied to the adsorbent material before or after it is placed in the column to form a bed. An amount of a first composition (feed) of known composition and containing at least two different compounds is applied to the top of the column. The level of the first composition may be allowed to sink to into the top of the bed. Suitable solvents are applied to the column to selectively elute compounds while collecting column effluent.

A fraction collector is suitable for obtaining fractions of the effluent which may be analyzed to determine the effectiveness of the solvents applied in separating the first composition into fractions selectively enriched in compounds contained in the first composition. The concentrations of the compounds in the fractions can then be plotted as in FIGS. 1, 2, 5, 6 and 7 to provide guidance in optimizing the solvents applied.

A cycle test is a test to determine the robustness of an adsorbent in a given application. A cycle test consists of sequentially running feed, rinse (if needed), elution by one or more solvents, allowing the solvent to carrying at least one separated component of the feed to pass out of the column, followed by a rinse (if needed) at a given flow rate through a single bed of adsorbent material. Each liquid is passed through the column for differing amounts of time, depending on the application. The particle size of the adsorbent is determined before and after the cycle test. The cycle tests determine: 1) change in performance of an adsorbent over a certain number of cycles; and 2) the physical degradation of the adsorbent particle over a certain number of cycles.

The present method of enriching a composition in compounds containing unsaturated carbon chains utilizes simulated moving bed chromatography. Several chromatographic beds, columns or parts thereof are aligned in a series wherein a feedstock flows through any number of chromatographic devices. An arrangement of valves at the top and bottom of each column direct the flow of eluants and products to subsequent columns in the same or a different zone. In this manner, the continuous movement of bed material is simulated. Thus, "zones" are defined not by the physical columns but by the function each column carries out at a given time.

In a complete cycle, each column has passed through each zone in the same sequence and continues. Feed and elution solvents can be applied at any column, and compound(s) to elute can be passed out from the series at any column through an outlet in an effluent stream. One of ordinary skill in the art can adjust parameters such as feed rate of the feedstock, solvent flow rate, desorbent rate, reload rate and step time to improve the separation.

In the present enrichment method, the simulated moving bed chromatography can comprise one or more zones. A zone is defined by the primary function of the chromatographic beds, columns or parts thereof. In a preferred embodiment, the present method utilizes four zones, wherein each zone comprises one or more chromatographic devices. In certain embodiments, one or more of the described zones can be replaced or eliminated. In other embodiments, one or more zone can be duplicated and operated sequentially with the other zones.

In one preferred embodiment, the simulated moving bed chromatography comprises preferably in sequence: a third elution zone, a second elution zone, an enrichment zone and a feed/adsorption/first elution zone.

Fatty acid methyl ester feed is applied continuously in the feed/adsorption/first elution zone, unsaturated FAME adsorb to the adsorbent bed, and an effluent enriched in saturated methyl esters and depleted of monounsaturated and polyunsaturated methyl esters is continuously eluted from the SMB in this zone and allowed to pass out of the SMB as an effluent labeled "Raffinate." The adsorbent bed passes into the enrichment zone, in which the remaining monounsaturated and polyunsaturated methyl esters on the bed are enriched to reach a higher concentration in the solvent flow. The adsorbent bed passes into the second elution zone, in which a second eluant solvent is applied continuously and a fraction enriched in monounsaturated methyl esters and depleted of saturated and polyunsaturated methyl esters is continuously eluted and allowed to pass out of the SMB as an effluent labeled "Product A." The adsorbent bed passes into the third elution zone, in which a third eluant solvent is applied continuously and a fraction enriched in polyunsaturated methyl esters and depleted of saturated and monounsaturated methyl esters is continuously eluted as "Product B" and allowed to pass out of the SMB as an effluent. In an embodiment, the enrichment zone can be eliminated.

In an embodiment using ion exchange resin, the simulated moving bed chromatography comprises preferably in sequence: A solvent A elution zone (third elution zone) in which a solvent A, such as isopropanol, is applied to the SMB, a solvent B elution zone (second elution zone), in which a solvent B, such as methanol, is applied to the SMB, an enrichment zone and a feed/adsorption/first elution zone.

What is meant by an "elution zone" is a zone in which a compound of a given degree of unsaturation is caused to dissociate from the resin bed by the application of a solvent. After the compound has eluted from the resin, it can be passed out of the SMB device as an effluent. In an embodiment, the enrichment zone can be eliminated.

In one embodiment using conditioned alumina, the simulated moving bed chromatography comprises preferably in sequence: A third elution zone in which heptane is applied to the SMB, a second elution zone, in which ethyl acetate is applied to the SMB, an enrichment zone and a feed/adsorption/first elution zone. What is meant by an elution zone is a zone in which a compound is caused to dissociate from the conditioned alumina bed by the application of a solvent. After the material has eluted from the resin, is can be passed out of the zone into the next zone, or it can be passed out of the SMB device as an effluent. In an embodiment, the enrichment zone can be eliminated.

The number of chromatographic beds, columns or parts thereof contained in the series can be unlimited. The present method can be optimized using the parameters stated above to improve product yield.

Another variable useful for optimizing the present method is the number of chromatographic devices used in the series. Within the series, each zone can have an optimized number of chromatographic devices. Thus, the present method is no way limited to a certain number of chromatographic devices.

Within the series of chromatographic devices, there are one or more zones as described above. Each zone contains an independent number of chromatographic devices.

The preferred embodiment is not limited to any number of chromatographic devices because the method is scalable, wherein the process parameters are readily scalable by one of ordinary skill in the art. One of the parameters is the unlimited number of chromatographic devices in a series and the number within each zone in the series.

The present invention is also directed to any one of the above methods, wherein the operation is sequential or continuous. Preferably, any of the above methods of the present method is conducted as a continuous process.

EXAMPLES

Example 1

Pulse Test of Argentized Cationic Resin

Mitsubishi EXC04 resin (Mitsubishi Chemical Corp. Tokyo, Japan) was ground to particles of 90-150 microns. The resin was then packed into a column and rinsed with 3 bed volumes (BV) of deionized water, after which the resin was argentized by passing 20 BV of a solution of 5% silver nitrate through the resin column. This was followed by a 4 BV deionized water rinse and then dried by thorough rinsing with dry methanol to produce a column containing a first argentized adsorbent. The first argentized adsorbent was then used to perform a pulse test on Soygold 1100, a commercially available mixture of soy fatty acid methyl esters (FAME) (Ag Environmental Products L.L.C., Omaha, Neb.; the SME/UME ratio of Soygold is 0.193).

A pulse test was carried out at ambient temperature using a 15 mm×600 mm jacketed glass column loaded with 100 milliliters of first argentized adsorbent. The feed material (Soygold 1100, 2 ml) was added onto the top of the column and allowed to drain so that the liquid level was equal to the top of the first argentized adsorbent bed. Methanol (99+%) was then pumped into the top of the column as an eluant at a flow rate of 5 ml/min. and the effluent was collected in a fraction collector.

Separation between the saturated FAME (Sats) and some of the unsaturated FAME took place (FIG. 1). Unsaturated FAMEs in FIG. 1 include oleic acid methyl ester (C18:1), linoleic acid methyl ester (C18:2), and linolenic acid methyl ester (C18:3). By collecting effluent as fractions eluted at 0.8 to 1 bed volumes, a fraction enriched in Sats and C18:1 FAME and devoid of 18:2 FAME was obtained. Alternatively, by starting to collect effluent at 1.2 bed volumes, a fraction enriched in C18:2 and depleted of Sats and C18:1 FAME was obtained.

Example 2

Pulse Test of Argentized Cationic Resin

Figure 2:
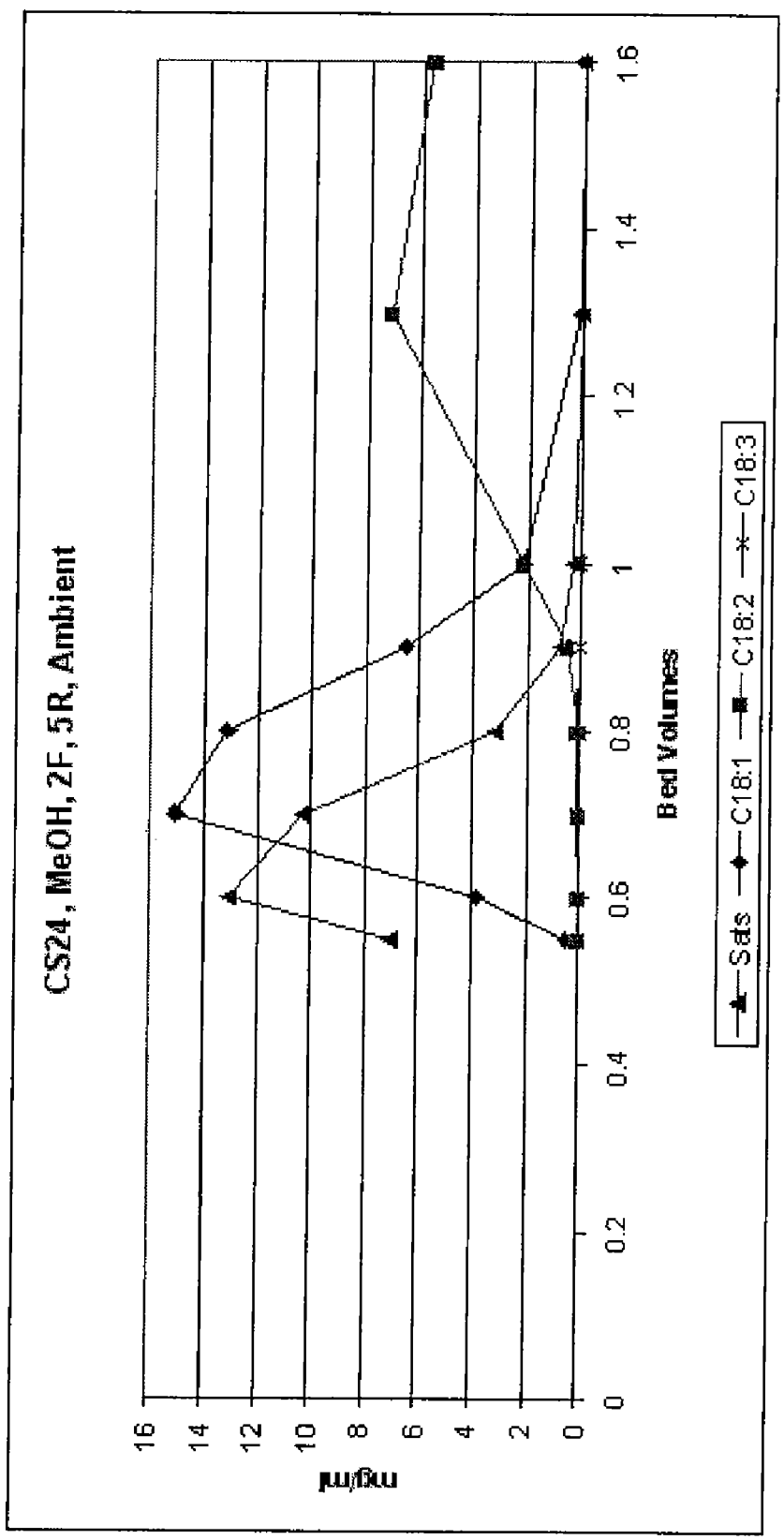
FIG. 2 depicts an elution profile of a pulse test for the separation of soy fatty acid methyl esters on argentized cationic CS24 resin from Example 2 eluted with methanol and effluents enriched in FAME of varying degrees of unsaturation are collected.

Finex CS 24 (Finex Ltd., Kotka, Finland) was argentized as in Example 1 to form a second argentized adsorbent and used in a pulse test as in Example 1. Elution of Soygold 1100 FAMEs developed after a smaller volume of eluant, but more tailing took place with this second argentized adsorbent than in Example 1 (FIG. 2). A fraction enriched in C18:2 FAME and depleted of Sats and C18:1 FAME could be obtained by collecting the effluent starting at 1.3 bed volumes.

Example 3

Simulated Moving Bed Chromatography of Argentized Cationic Resin

Figure 3:
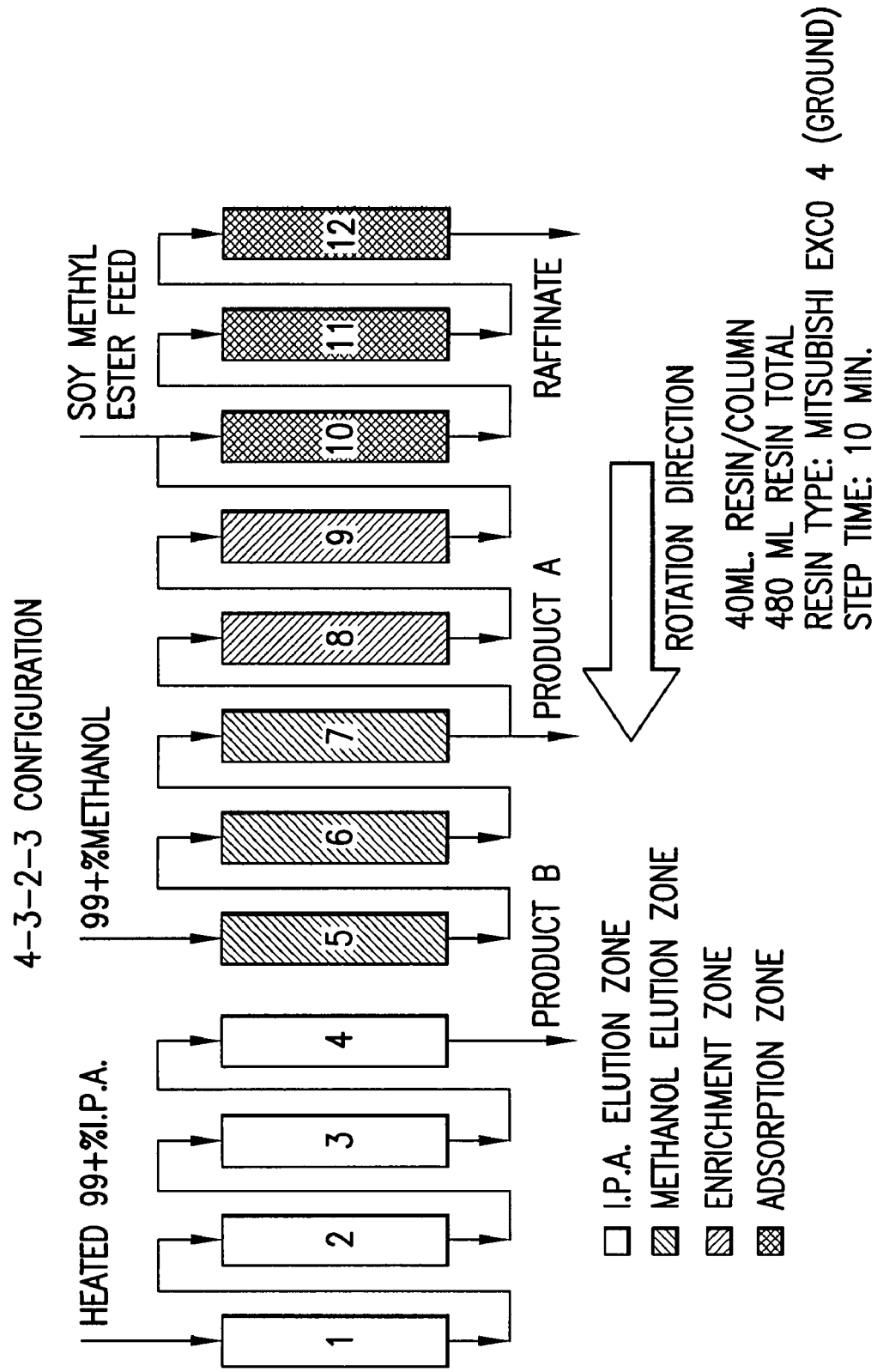
FIG. 3 depicts a simulated moving bed system in a 4-3-2-3 configuration used for separation of soy fatty acid methyl esters on argentized EXC04 resin from Example 3 eluted simultaneously with methanol and isopropanol and effluents enriched in FAME of varying degrees of unsaturation are collected.

Based on the information obtained in Example 1, Simulated Moving Bed Argentation Chromatography was carried out in a 12-column AST type simulated moving bed (SMB) system (FIG. 3) using glass columns containing 40 milliliters, each, of argentized ion exchange strong acid cation resin (in this case Mitsubishi EXC04, ground and argentized as in Example 1).

Feed containing compounds to be separated (in this case, Soygold 1100 FAME) was continually fed to the system, which was configured in a 4-3-2-3 configuration. Two elution solvents were simultaneously fed into different zones. As the operation proceeded, valves changed the point at which feed and solvents were applied, simultaneous to changing the points at which the effluent streams were removed. In this manner, movement of the bed is simulated.

The SMB was operated with 3 columns in the adsorption zone. In this zone feed was introduced into the system. Unsaturated methyl esters (monounsaturated and polyunsaturated) in the feed adsorbed onto the adsorbent, while saturated methyl esters continued to move forward with the solvent flow and were eluted from the SMB apparatus in an effluent stream called "Raffinate." The Raffinate was a composition enriched in saturated methyl esters and depleted of monounsaturated and polyunsaturated methyl esters.

The unsaturated methyl ester flow, now depleted of saturated methyl esters, continued to flow into the enrichment zone, which comprised 2 columns. The enrichment zone may be used to concentrate or enrich a desired compound; this can be effected by applying a lower flow rate than the eluant flow rates. Thus, the concentration of unsaturated methyl esters eluant was increased in this zone.

The next zone (methanol zone) comprised three columns. A continuous stream of methanol was provided to the methanol zone. In this zone, a stream enriched in monounsaturated methyl esters and depleted of saturated and polyunsaturated methyl esters was eluted as "Product A" (purified product) and passed out of the SMB as an effluent stream.

A continuous stream of isopropanol (IPA) was applied to the isopropanol zone, which comprised four columns, and an additional degree of separation not obtained in Example 1 was carried out. Polyunsaturated methyl esters eluted from the adsorbent as "Product B" and passed out of the SMB as an effluent stream. The IPA also acted as a wash to prepare the columns for subsequent loading of feed as a new cycle began. The Feed, Methanol, and IPA were fed continuously, and the Raffinate, Product A and Product B effluents passed out of the SMB continuously and simultaneously, so that the process operated in continuous fashion.

The composition of the feed and the product purity (based on percent unsaturates) are given in Table 1. The step time was 10 minutes. The temperature of the system was ambient except the IPA which was at 55° C. The flow rates were as follows:

| Feed: | 0.4 ml/min. | Enrich: | 3.0 ml/min. |
|---|---|---|---|
| Methanol: | 5.0 ml/min. | IPA: | 5.0 ml/min. |

TABLE 1

Purity and Yield

| | Purity (based on percent unsaturate FAME) | Yield (%) |
|---|---|---|
| Feed | 86.0 | — |
| Raffinate effluent | 78.3 | — |
| Product A effluent | 89.0 | 50.0 |
| Product B effluent | 84.4 | 0.5 |

Raffinate was lower in unsaturated FAME than the feed and thus had been enriched in saturated FAME.

Example 4

Simulated Moving Bed Chromatography with Argentized Cationic Resin

Figure 4:
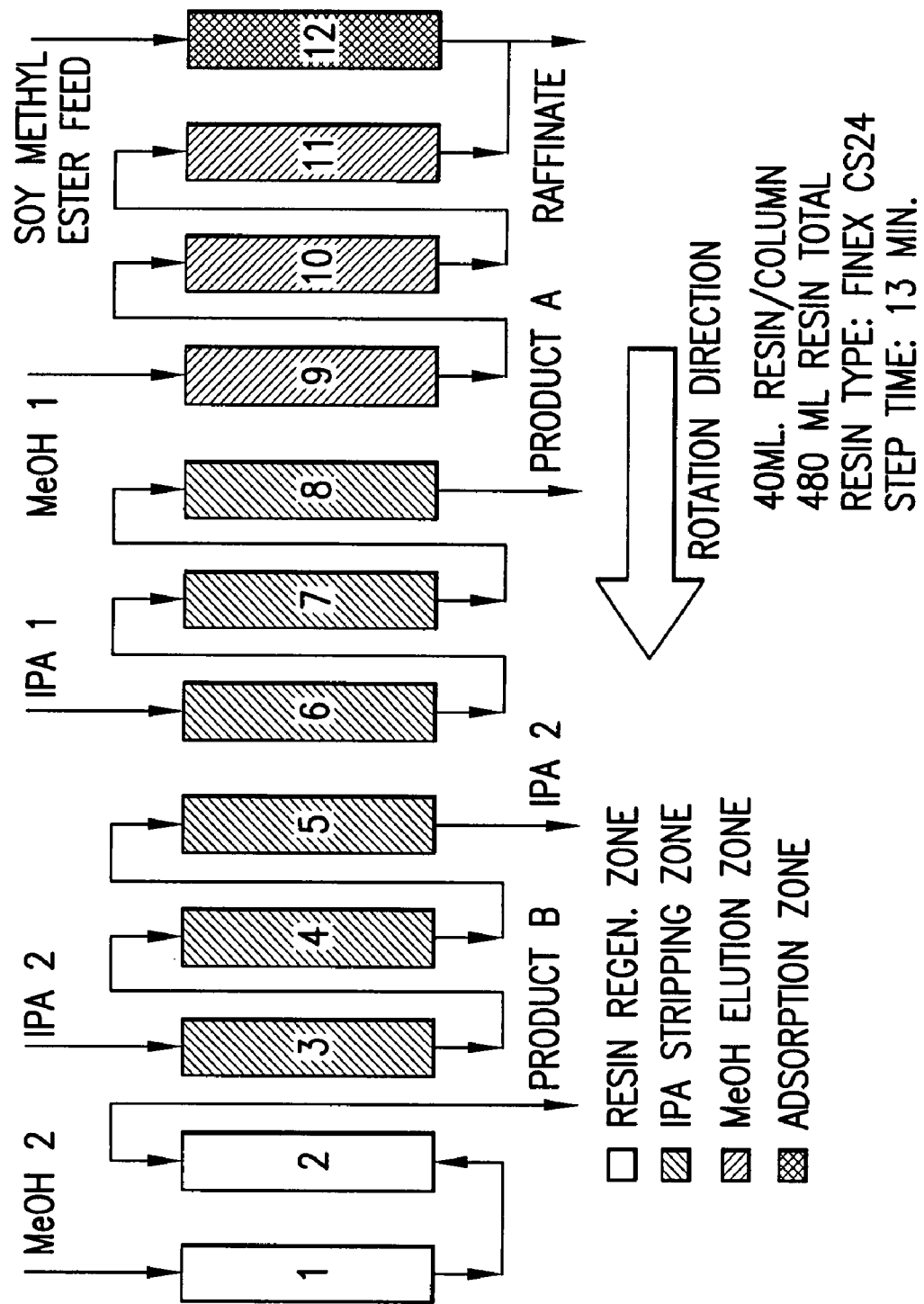
FIG. 4 depicts a simulated moving bed system in a 2-3-3-3-1 configuration used for separation of soy fatty acid methyl esters on argentized Finex CS24 resin from Example 4 eluted simultaneously with methanol and isopropanol and effluents enriched in FAME of varying degrees of unsaturation are collected.

Simulated Moving Bed Argentation Chromatography was carried out in a 12-column AST type simulated moving bed system (FIG. 4) using glass columns containing 40 milliliters, each, of argentized ion exchange strong acid cation resin (in this case Finex CS 24, argentized as in Example 1). The system was configured in a 2-3-3-3-1 configuration where there were 2 columns in the methanol 2 zone, which displaced the isopropyl alcohol already in the zone and prepared the columns in the zone to accept feed, 6 columns in the IPA zone (2 sets of three in series) in which IPA was applied to elute as "Product A" (enriched in monounsaturated FAME and depleted of saturated and polyunsaturated FAME) and "Product B" (enriched in polyunsaturated FAME and depleted of saturated and monounsaturated FAME); they were then passed out of the SMB as "Product A effluent" and "Product B effluent", respectively; 3 columns in the methanol 1 zone, which moved the saturates from the feed forward and causes the saturated FAME to pass out of the SMB as an effluent called "Raffinate" (enriched in saturated FAME and depleted of unsaturated (monounsaturated and polyunsaturated) FAME) and 1 column in the adsorption zone in which feed was loaded onto the column.

Soygold 1100 was continuously fed to the top of column 12 in the Adsorption zone. The step time was 13 minutes. The temperature of the system was ambient, except the IPA which was at 55° C. The flow rates were as follows:

| Soygold FAME: | 0.1 ml/min. | Methanol 2: | 5.8 ml/min. |
|---|---|---|---|
| Methanol 1: | 3.0 ml/min. | IPA: | 10.6 ml/min. |

TABLE 2

Purity and Yield

| | Purity of Unsaturates (%) | Yield (%) |
|---|---|---|
| Feed | 86.0 | — |
| Raffinate | 69.7 | — |
| Product A | 97.3 | 52.2 |
| Product B | 100.0 | 3.1 |

A raffinate effluent depleted in unsaturated FAME (and thus enriched in saturated FAME), a fraction effluent enriched in monounsaturated FAME (Product A) and an effluent enriched in polyunsaturate FAME (Product B) passed out of the SMB and were analyzed (Table 2).

Raffinate effluent was depleted of unsaturated FAME, Product A effluent was enriched in monounsaturates, and product B effluent contained only the desired polyunsaturates.

Example 5

Pulse Test of Argentized Alumina

Granular basic alumina (DD-6), Almatis AC, INC., Vidalia, La.) was slurried in water and the pH of the suspension was adjusted to 7.2 to neutralize the slurry. The slurry was filtered and the granular alumina filter cake was dried overnight at 85° C., then baked at 650° C. for 2 hours (during this treatment, the surface area of the alumina decreased from about 350 square meters/gram to around 150 square meters/gram). The baked alumina was then slurried in a 5 wt % solution of silver nitrate in deionized water. This slurry was dried overnight at 85° C., then baked at 180° C. for 2 hours to yield a first argentized alumina adsorbent which was pale in color.

The first argentized alumina adsorbent was packed into a column as in Example 1 and a pulse test of Soygold 1100 FAME was carried out as in Example 1, except that elution was carried out in two stages (with two solvents in series). The pulse test was carried out immediately after the argentation treatment, so that no conditioning was applied. No visible darkening had occurred.

After the Soygold 1100 pulse was loaded into the top of the column as in Example 1, two bed volumes (BV) of heptane was passed through the bed of first argentized alumina adsorbent. Subsequently, 3.5 bed volumes of ethyl acetate were passed through the bed.

Figure 5:
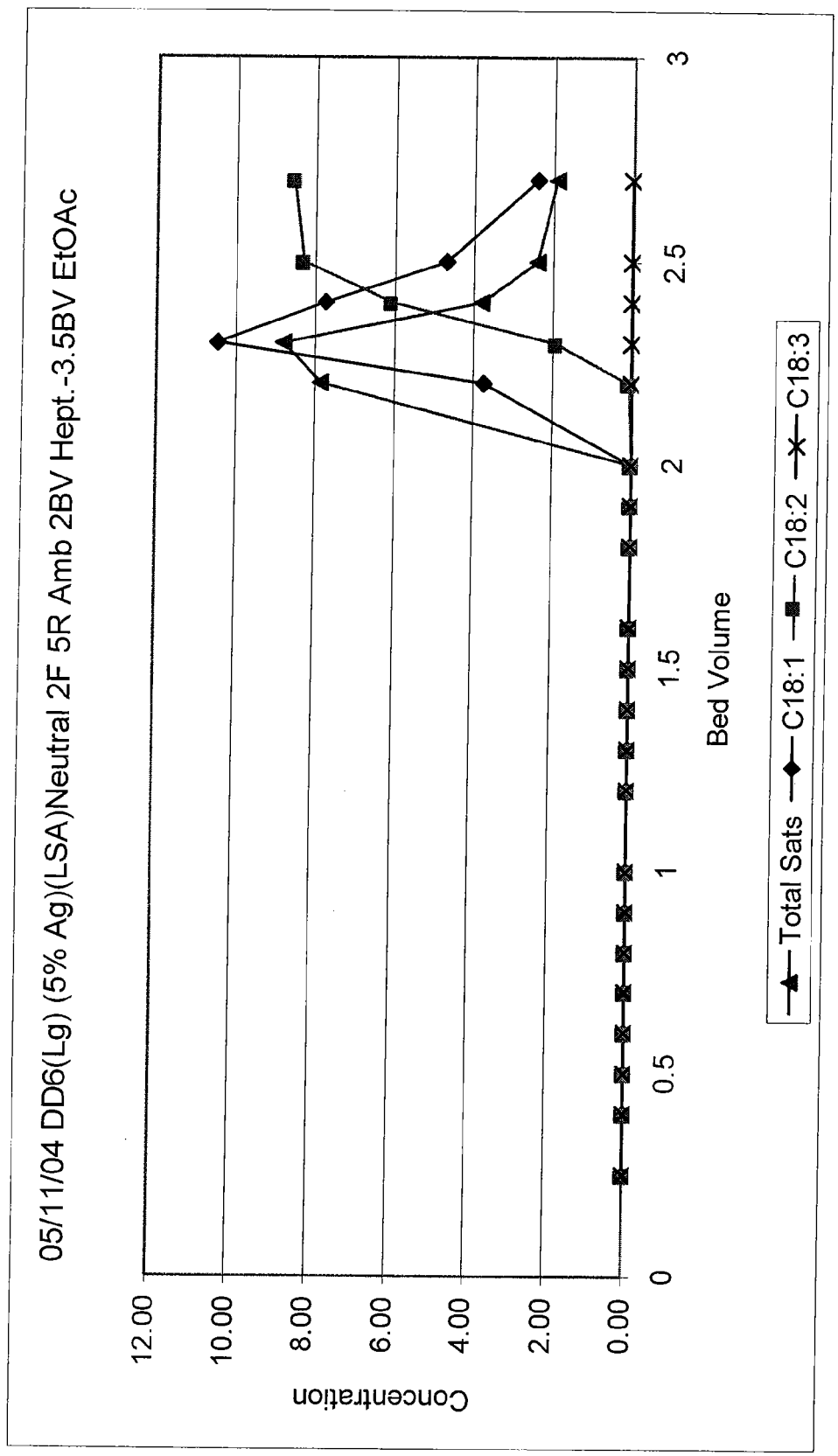
FIG. 5 depicts an elution profile of a pulse test for the separation of soy fatty acid methyl esters on argentized granular neutral alumina from Example 5 eluted sequentially with heptane and ethyl acetate and effluents enriched in FAME of varying degrees of unsaturation are collected.
Figure 6:
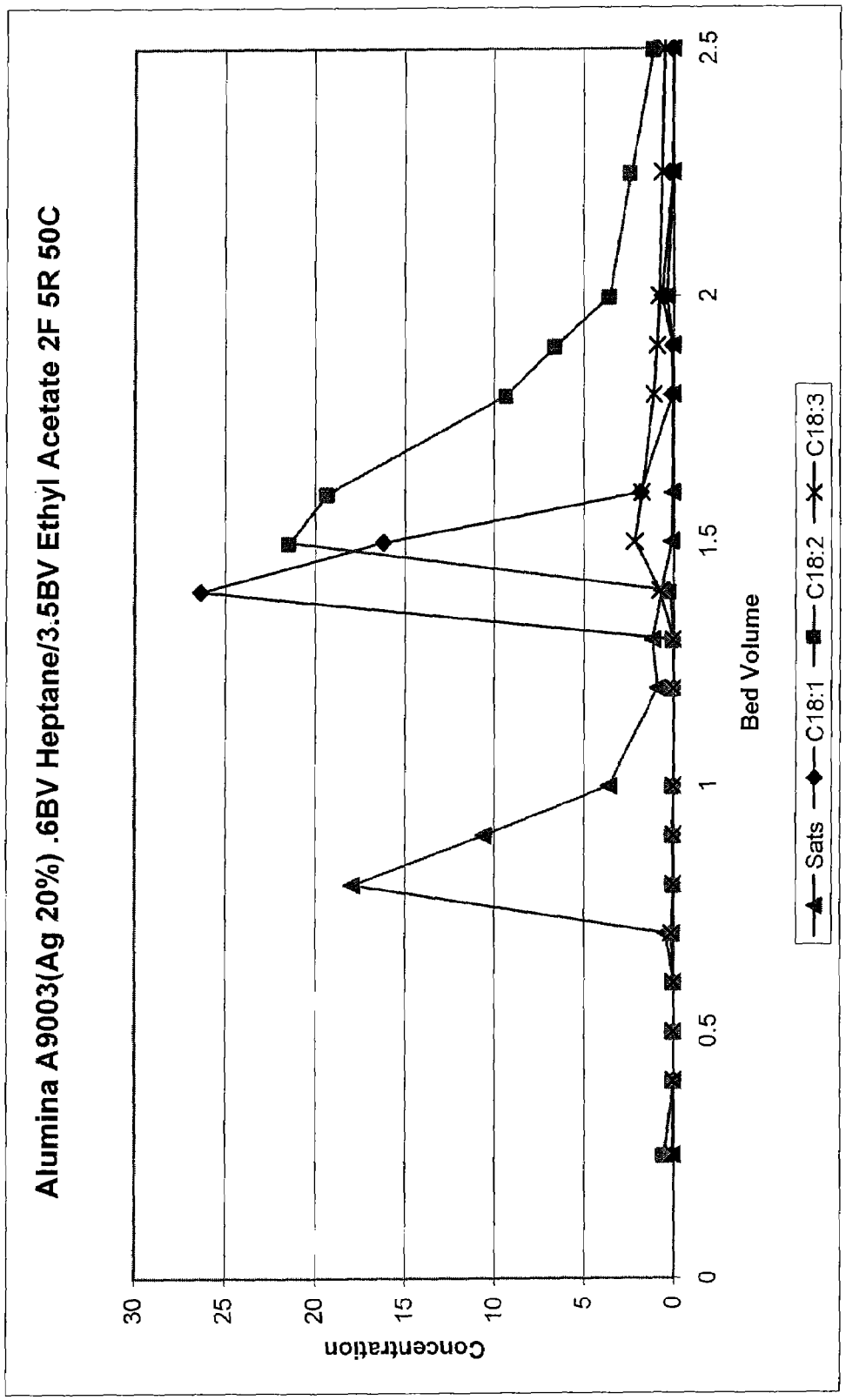
FIG. 6 depicts an elution profile of a pulse test for the separation of soy fatty acid methyl esters with conditioned granular neutral alumina from Example 6 eluted sequentially with heptane and ethyl acetate and effluents enriched in FAME of varying degrees of unsaturation are collected.

No elution of FAME took place with heptane; however, when ethyl acetate was passed through the bed, immediate selective elution of a very small fraction enriched in saturated FAME (Total Sats) and monounsaturated FAME (C18:1) and devoid of polyunsaturated FAME (C18:2) was observed at 2-2.2 bed volumes (FIG. 5; Concentration on the ordinate axis is given in grams/kilogram).

Thus, effluent fractions collected before about 2.2 bed volumes were devoid of polyunsaturated FAME (C18:2 and C18:3 in this example). However, an effluent fraction containing substantially saturated FAME (Total Sats) and devoid of unsaturated FAME was not obtained. Without conditioning, argentized alumina was ineffective at providing a desired separation of saturated FAME from monounsaturated FAME.

Example 6

Pulse Test of Conditioned Argentized Alumina

Neutral alumina (SIGMA A9003, Sigma-Aldrich, St. Louis, Mo.) having a surface area of approximately 150 square meters/gram was slurried in a 20% w/w solution of silver nitrate and dried overnight at 85° C. The adsorbent was loaded in heptane into a 100 ml jacketed column and stored about 72 hours in heptane to produce a first conditioned argentized alumina adsorbent. The first conditioned argentized adsorbent had darkened visibly after conditioning with heptane.

The column temperature was raised to 50° C., and Soygold 1100 (2 ml) was loaded onto the column as in Example 1. Elution was carried out with two solvents as in Example 5, except with a smaller volume of a first solvent of heptane (0.6 BV), followed by a second solvent (ethyl acetate, 3.5 BV).

A fraction highly enriched in saturated FAME and devoid of monounsaturated FAME and polyunsaturated FAME eluted at 0.7-1.3 BV (FIG. 6) and passed out of the SMB as an effluent. A fraction enriched in unsaturated FAME and devoid of saturated FAME and polyunsaturated FAME eluted at 1.3-1.4 BV and passed out of the SMB as an effluent. In addition, a fraction enriched in polyunsaturated FAME and devoid of saturated FAME and very low in monounsaturated FAME was obtained by collecting effluent from the adsorbent from 1.6 to 2.5 bed volumes. Concentration on the ordinate axis is given in grams/kilogram.

A second pulse test on the first conditioned argentized alumina adsorbent was carried out. A first effluent was collected until approximately 1.2 BV, and a second effluent was collected from about 1.2 to about 2.5 BV, and purity and yields were calculated. Unsaturates include C18:1, C18:2 and C18:3.

TABLE 3

Purity and yield

|  | Sats (g) | C18:1 (g) | C18:2 (g) | C18:3 (g) | PURITY (%) | YIELD (%) |
|---|---|---|---|---|---|---|
| Feed | 0.29 | 0.40 | 0.96 | 0.14 | 86.0% Unsaturates | |
| First effluent | 0.23 | 0.00 | 0.00 | 0.00 | 99.3% Sats | |
| Second effluent | 0.03 | 0.37 | 0.98 | 0.15 | 97.8% Unsaturates | 100.2 |

The first effluent was enriched in saturated FAME and devoid of unsaturated FAME. The second effluent was enriched in unsaturated FAME and contained a very small amount of saturated FAME.

Example 7

Selectivity Coefficients

Selectivity coefficients of several adsorbents were calculated from pulse tests carried out as in Example 5 except that 2 BV of ethyl acetate were applied instead of 3.5 BV. Granular DD-6 Basic alumina (Almatis AC, Inc., Vidalia, La.) was argentized as received in the basic form and conditioned for one test. In another test the pH of DD6 was adjusted using nitric acid to provide neutral alumina before argentizing and conditioning. Sigma acidic alumina (A-8753) was argentized as received and conditioned. Adsorbents were oven-dried at 85° C. overnight before being argentized with silver nitrate solutions (indicated in Table 4) as in Example 1.

Following argentization treatment with silver nitrate, adsorbents were dried at 85° C., then heated at 180° C. for two hours. All adsorbents were packed into columns. Argentized adsorbent (Row 1) was pale in color and was used in a pulse test directly after preparation. Conditioned adsorbents (Rows 2-5) were conditioned by incubating in heptane in the columns for 72 hours before pulse tests and had darkened in color after conditioning.

ditioned basic alumina had slightly better selectivity but was still low. Conditioned neutral alumina demonstrated the highest selectivity, followed by the acidic form and the conditioned adsorbent.

Figure 7:
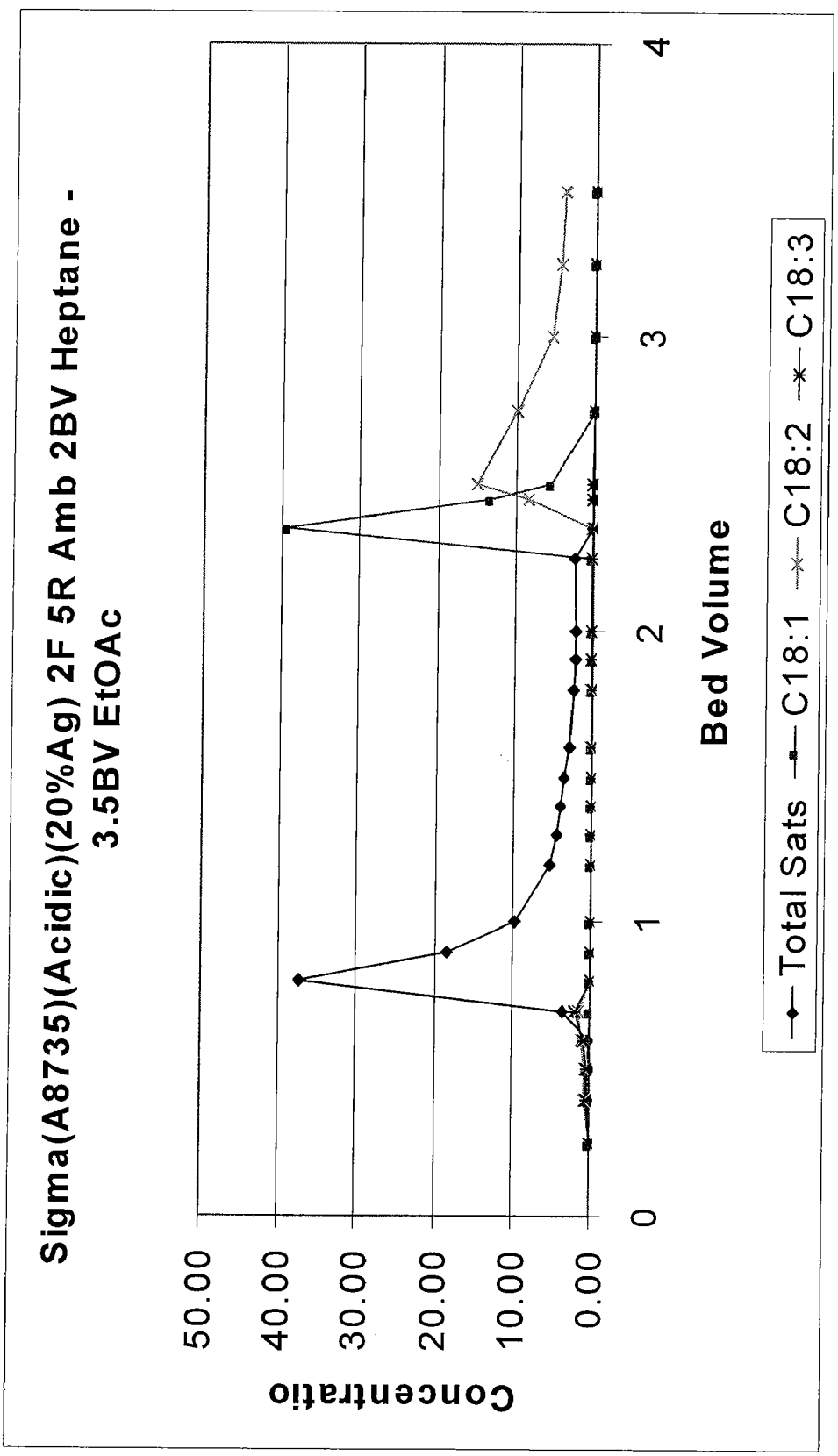
FIG. 7 depicts an elution profile of a pulse test for separation of fatty acid methyl esters with conditioned acidic alumina from Example 7 eluted sequentially with heptane and ethyl acetate and effluents enriched in FAME of varying degrees of unsaturation are collected.

The elution profile for conditioned acidic alumina (Row 4 of Table 4) is given in FIG. 7 (Concentration on the ordinate axis is given in grams/kilogram). A fraction enriched in saturated FAME and virtually devoid of monounsaturated FAME and polyunsaturated FAME could be obtained by collecting effluent at 0.6-2.2 BV. In addition, a fraction enriched in monounsaturated FAME and containing very little saturated FAME or polyunsaturated FAME was obtained by collecting effluent at 2.2-2.3 bed volumes. A fraction enriched in polyunsaturated FAME and depleted of saturated FAME and monounsaturated FAME was obtained by collecting effluent at 2.3-3.5 BV.

Example 8

Pulse Tests of Conditioned Argentized Spherical Alumina

Spherical alumina (LaChemCo, Gramercy, La.) having a Hunter L value of 82.58 was slurried with water and neutralized with concentrated nitric acid. Neutral was defined as the point at which the water portion of the slurry had been adjusted to pH 7.0. The slurry was dried overnight at 85° C. The dried neutralized spherical alumina was then slurried with a solution of 20% silver nitrate (AgNO$_3$) and the slurry was dried overnight at 85° C. and placed in an oven at 180° C. for two hours, cooled to form an argentized spherical alumina adsorbent. The Hunter L color was determined to be 69.27 (Table 5).

The argentized spherical alumina adsorbent having a Hunter L value of 69.27 was divided into four lots, loaded into four identical jacketed glass columns as in Example 1 and each adsorbent bed was rinsed with heptane.

TABLE 4

Selectivity of argentized adsorbent and argentized conditioned adsorbents

| Row | Adsorbent | Concentration of silver nitrate solution (%) | Selectivity (B) in heptane elution (0–2 BV) | Selectivity (B) in ethyl acetate elution (2–4 BV) |
|---|---|---|---|---|
| 1 | Argentized adsorbent (no conditioning, as in example 5) | 5 | 1.06 | 0.37 |
| 2 | Conditioned basic alumina | 10 | 0.809 | 0.202 |
| 3 | Conditioned neutral alumina | 20 | 0.01 | 36.61 |
| 4 | Conditioned acidic alumina | 20 | 0.03 | 10.41 |
| 5 | Conditioned adsorbent (as in example 6) | 5 | 0.01 | 4.61 |

The selectivity of argentized alumina adsorbent without conditioning (row 1) was close to 1.000 and thus low. Con- The first lot (Lot A) was not conditioned, but was immediately subjected to a pulse test (40° C.) with 2 ml Soygold 1100 as in Example 1, with 1.5 BV heptane and 3.5 BV of ethyl acetate. The selectivity coefficient value was calculated to be 1.06 for the heptane fraction and 0.37 for the ethyl acetate fraction. The SME/UME ratios for Lot A were 0.17 (0-2 BV) and 0.359 (2-4 BV).

The second lot (Lot B) was conditioned by incubating in heptane for 72 hours until the argentized adsorbent was observed to have darkened visibly, then the conditioned argentized spherical alumina adsorbent was removed from the column and divided into three parts. Part B1 was desolventized in air at room temperature. Part B2 was desolventized in air at room temperature, then heated in an oven at 85° C. for one hour. Part B3 was washed with sufficient ethyl acetate to displace heptane, desolventized in air at room temperature and heated in an oven at 85° C. for one hour. After cooling, the Hunter L color values were measured.

The third lot (Lot C) was conditioned by incubating in heptane for 72 hours until the adsorbent darkened visibly to grey, and a pulse test of Soygold 1100 was carried out with 1.5 BV heptane and 3.5 BV of ethyl acetate. The SME/UME ratios were 13.0 (0-2 BV) and 0.06 (2-4 BV). After the pulse test, the selectivity value was calculated and the argentized alumina was removed from the column and air dried. The Hunter L color values were then measured. Lot C had darkened to a Hunter L value of 53.85 after conditioning and the pulse test.

The fourth lot (Lot D) was treated as Lot A, except that the argentized spherical adsorbent was conditioned by incubating in heptane for 120 hours before a pulse test was run with 1.5 BV heptane and 3.5 BV of ethyl acetate. Excellent selectivity coefficients were obtained (0-2 BV (heptane): 0.0; 2-4 BV (ethyl acetate): 298.5). After the pulse test was completed, the conditioned argentized spherical alumina adsorbent was removed from the column and air dried, and the Hunter L color values were measured.

TABLE 5

Hunter L color values

| Hunter L color values | L |
|---|---|
| Granular alumina as received | 82.58 |
| Lot A Argentized granular alumina (before conditioning) | 69.27 |
| Lot B1 (heptane-conditioned) | 60.51 |
| Lot B2 (heptane-conditioned and heated) | 60.43 |
| Lot B3 (heptane-conditioned, washed with ethyl acetate and heated) | 33.96 |
| Lot C (heptane conditioned (72 hours) and used in a pulse test) | 53.85 |
| Lot D (heptane conditioned (120 hours) and used in a pulse test) | 27.97 |

Example 9

Pulse Test of Conditioned Spherical Alumina

In examples 5, 6, and 7, good separation was obtained with granular alumina. However, the material was not as robust as desired and deteriorated during use, causing development of fine particles after 2 or 3 cycles. This could create problems due to increases in pressure drop across the column during use. "Spherical Alumina" was obtained from LaChemCo (Gramercy, La.). The surface area was 312 m$^2$/gm, the total pore volume was 0.1519 cc/gm. The free moisture content was 20.9%, and the total loss on ignition (LOI) was 31.7%.

The pH of Spherical Alumina was adjusted as in Example 5 and heated overnight at 85° C. to dry. The dried spherical alumina was slurried in 5% silver nitrate and deionized water, and heated overnight at 85° C. to dry. The adsorbent material was then heated at 180° C. for 2 hours to yield argentized spherical alumina. After preparation, the Hunter L color value of this argentized spherical alumina adsorbent was 69.27.

The argentized Spherical Alumina adsorbent was loaded into a column in heptane and conditioned in heptane for 72 hours to form a conditioned argentized spherical alumina adsorbent that had darkened visibly.

Figure 8:
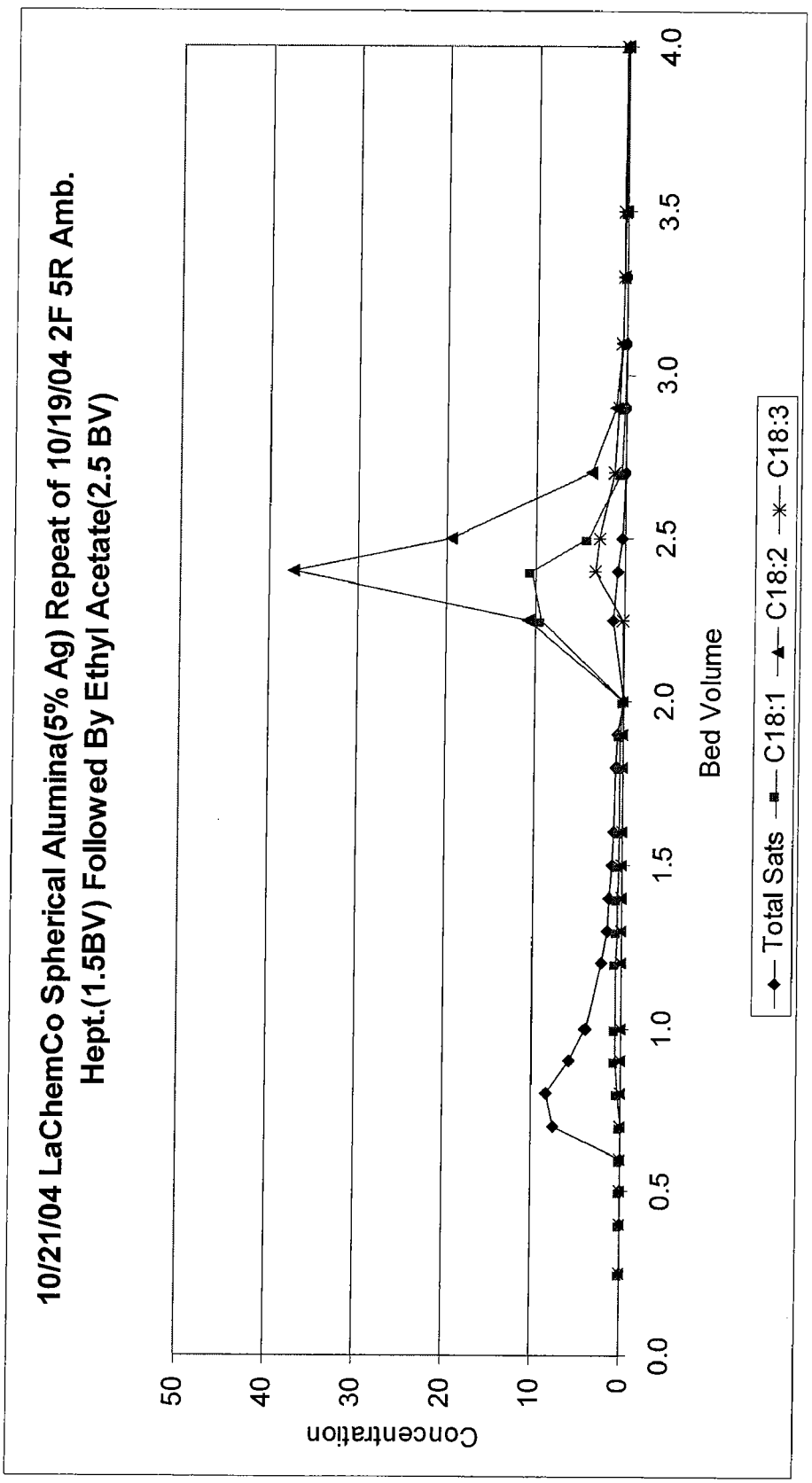
FIG. 8 depicts an elution profile of a pulse test for the separation of soy fatty acid methyl esters with conditioned spherical alumina from Example 8 eluted sequentially with heptane and ethyl acetate and effluents enriched in FAME of varying degrees of unsaturation are collected.

A pulse test with Soygold 1100 was carried out as in example 5 except that 1.5 BV of heptane was applied, followed by 2.5 BV of ethyl acetate. Excellent selectivity and SME/UME ratios were obtained (Table 6). A fraction enriched in saturated FAME (SME) and depleted of monounsaturated FAME and polyunsaturated FAME was obtained by collecting effluent at 0.6-2.0 BV. A fraction depleted of saturated FAME and enriched in unsaturated FAME (C18:1+C18: 2+C18:3; UME) was obtained by collecting effluent at 2.0-3.0 BV (FIG. 8; Concentration on the ordinate axis is given in grams/kilogram).

TABLE 6

Selectivity and SME/UME ratios of Spherical Alumina

| 0–2 BV Heptane Selectivity | 0.013 |
|---|---|
| 0–2 BV Heptane SME/UME | 7.053 |
| 2–4 BV EtOAc Selectivity | 11.529 |
| 2–4 BV EtOAc SME/UME | 0.024 |

Example 10

Spherical Alumina Particle Size

A cycle test of conditioned argentized Spherical Alumina (17 ml in packed column) conditioned substantially as in Example 9 was carried out for 102.5 cycles to determine the robustness of the adsorbent. In a given cycle, feed (Soygold 1100) was fed to the top of the column for 24 seconds, followed by heptane eluant for 30 minutes; this was followed by ethyl acetate eluant for 50 minutes and then a heptane wash for 60 minutes (all at a flow rate of 2 ml/min).

Particle size analysis was done on the adsorbent before and after the cycle test. The particle size of the conditioned Spherical Alumina was substantially unchanged after 102.5 cycles, indicating robustness of the adsorbent (Table 7).

TABLE 7

Particle sizes of Spherical Alumina before and after cycle tests.

| Particle Diameter | ≦10% | ≦50% | ≦90% |
|---|---|---|---|
| Before test | 242 μm | 397 μm | 581 μm |
| After 102.5 cycles | 310 μm | 460 μm | 666 μm |

Example 11

Simulated Moving Bed Chromatography with Conditioned Argentized Spherical Alumina Adsorbent and Two Elution Streams Spherical alumina is slurried with water and neutralized with concentrated nitric acid. Neutral is defined as the point at which the water portion of the slurry has been adjusted to pH 7.0. The slurry is dried overnight at 85° C. The dried neutralized spherical alumina is then slurried with a solution of 20% silver nitrate (AgNO$_3$) and the slurry is dried overnight at 85°

C., placed in an oven at 180° C. for two hours, and cooled to form an argentized spherical alumina adsorbent.

Figure 9:
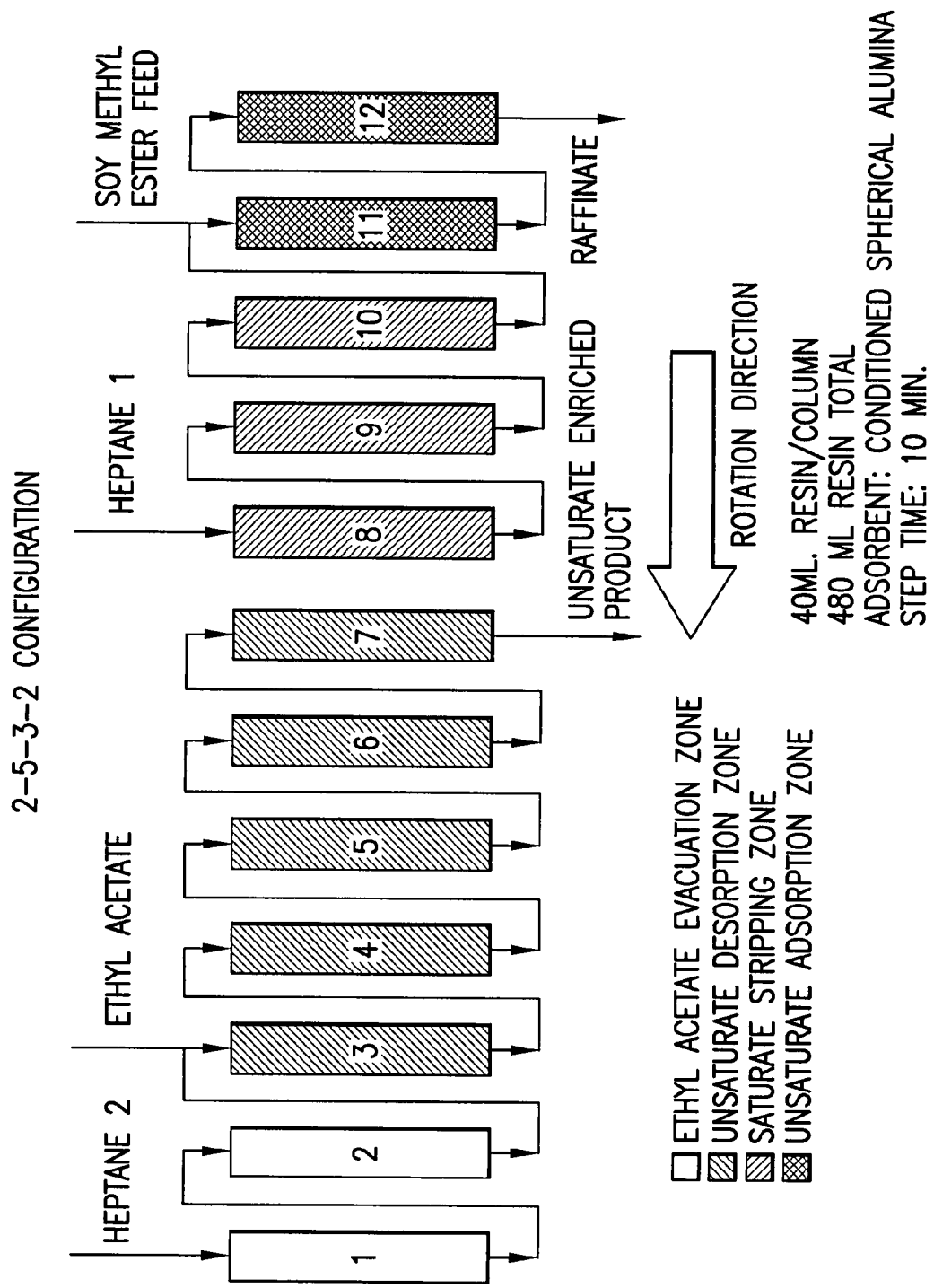
FIG. 9 depicts a simulated moving bed system in a 2-5-3-2 configuration used for proposed separation of soy fatty acid methyl esters on argentized spherical alumina. The column is eluted simultaneously with heptane and ethyl acetate, and effluents enriched in FAME of varying degrees of unsaturation are collected.

The argentized spherical alumina adsorbent is packed into 12 glass columns, each containing 40 milliliters, and incubated in heptane for 72 hours to provide a conditioned argentized spherical alumina adsorbent. Simulated Moving Bed Argentation Chromatography is carried out in a 12-column AST type simulated moving bed (SMB) system (FIG. 9) using glass columns containing 40 milliliters, each, of adsorbent material.

Feed containing compounds to be separated (in this case, Soygold 1100 FAME) is continually fed to the system, which is configured in a 2-5-3-2 configuration as follows: 2 columns are in an ethyl acetate evacuation zone (this zone displaces ethyl acetate from column and prepares it for adsorption zone); 5 columns are in a second desorption zone (this zone elutes the unsaturated methyl esters, as well as strips any remaining material from the zone, passing both out of the SMB as an effluent); 3 columns are in a first stripping zone (this zone strips any remaining saturated methyl esters from the zone, leaving the unsaturated methyl esters adsorbed and passing an effluent enriched in saturated methyl esters out of the SMB); and 2 columns are in a feed/adsorption/raffinate zone (this zone allows for the adsorption of all unsaturated methyl esters while the heptane addition prohibits the adsorption of the saturated methyl esters) having an effluent stream in which an effluent enriched in saturated FAME is passed out of the SMB. The step time is 10 minutes. The temperature of the system is ambient in all zones except the unsaturated desorption zone (ethyl acetate). The flow rates are as follows:

| Feed: | 0.4–1.0 ml/min. | Ethyl acetate: | 2.0–4.0 ml/min. |
|---|---|---|---|
| Heptane 1: | 2.0–3.5 ml/min. | Heptane 2: | 1.0–3.0 ml/min. |

The use of heptane, in the saturate stripping zone and feed/adsorption/raffinate zone, causes the elution of a raffinate stream enriched in saturated FAME and depleted of unsaturated FAME (which are adsorbed on the adsorbent), and allows the raffinate to pass out of the SMB as an effluent. The ethyl acetate elution, in the second desorption zone, will cause the unsaturated FAME to desorb and the effluent stream exiting the column is enriched in unsaturated FAME and depleted of saturated FAME.

Example 12

Figure 10:
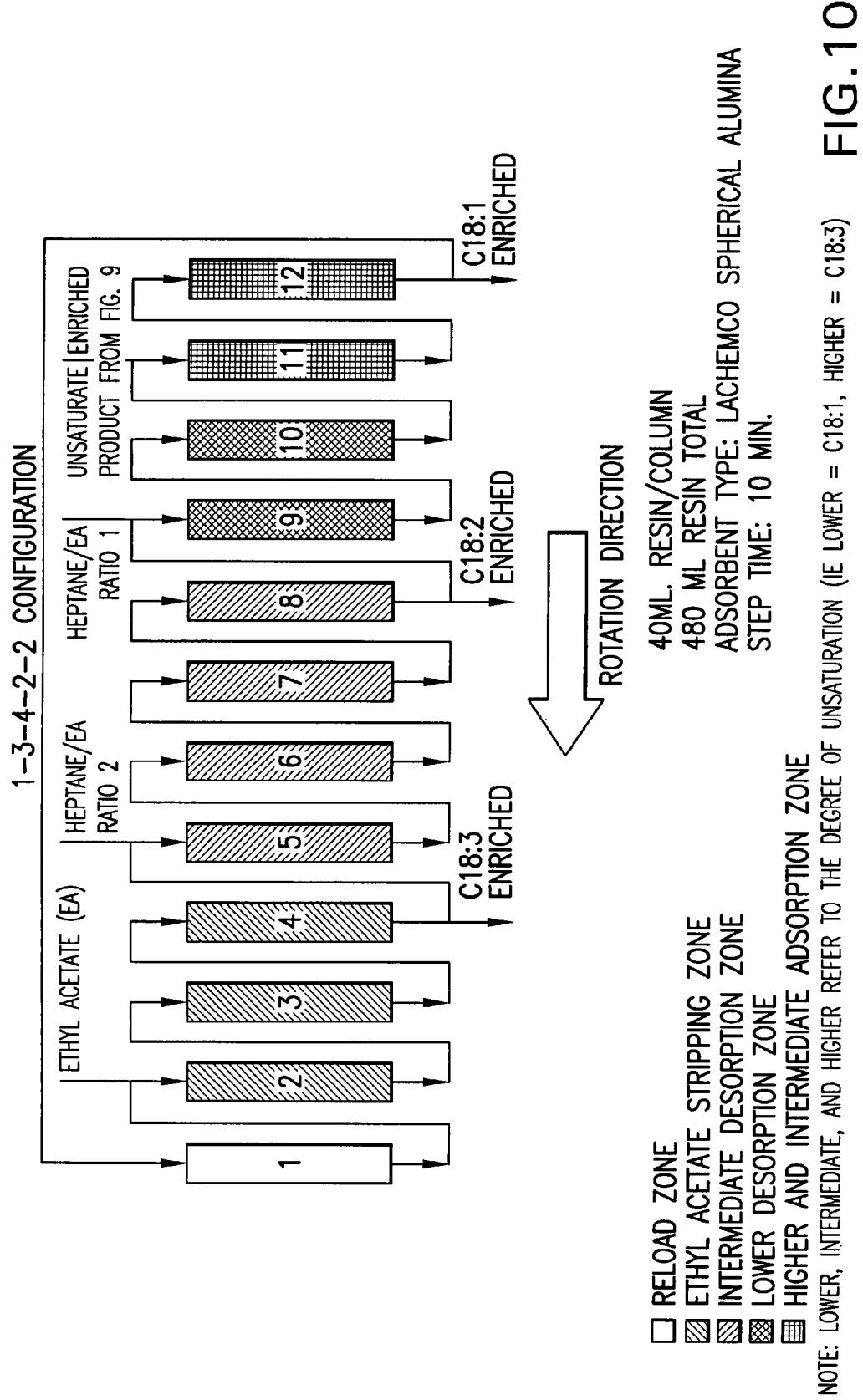
FIG. 10 depicts a simulated moving bed system in a 1-3-4-2-2 configuration used for proposed separation of unsaturated soy fatty acid methyl esters on argentized spherical alumina. The column is eluted with simultaneously with heptane and ethyl acetate eluants at two different ratios and ethyl acetate and effluents enriched in FAME of varying degrees of unsaturation are collected.

Simulated Moving Bed Chromatography with Conditioned Argentized Spherical Alumina Adsorbent and Three Elution Zones Conditioned argentized spherical alumina is prepared substantially as in Example 11 and Simulated Moving Bed Argentation Chromatography is carried out in a 12-column AST type simulated moving bed (SMB) system (FIG. 10) using glass columns containing 40 milliliters, each, of adsorbent.

Feed containing compounds to be separated (in this case, desolventized ethyl acetate effluent enriched in unsaturated FAME from the second desorption zone in example 11) is continually fed into column 11 of the SMB system, which is configured in a 1-3-4-2-2 configuration as follows: Column 1 is in the reload zone (this zone displaces ethyl acetate from column and prepares it for the feed/adsorption zone). Columns 2-4 comprise the ethyl acetate stripping zone (this zone elutes the more highly unsaturated FAME [C18:3], as well as strips any remaining material from the zone, allowing them to pass out of the SMB as an effluent stream enriched in C18:3 FAME). Columns 5-8 comprise the intermediate desorption zone (this zone desorbs [using heptane/EA at ratio 2] the intermediately unsaturated methyl esters [C18:2] from the zone, leaving the more highly unsaturated methyl esters adsorbed, and allows a fraction enriched in C18:2 to pass out of the SMB as an effluent).

Columns 9-10 comprise the lower desorption zone (this zone allows for the desorption of all monounsaturated methyl esters [C18:1] but the heptane/ethyl acetate ratio [ratio 1] permits the more highly unsaturated methyl esters to remain on the adsorbent, allowing a fraction enriched in monounsaturated FAME to pass out of the SMB as an effluent). Columns 11-12 comprise the higher and intermediate adsorption zone (this zone allows for the adsorption of the more highly unsaturated methyl esters [C18:2, C18:3] while the heptane/ethyl acetate ratio prohibits the adsorption of the components of lower degrees of unsaturation [C18:1]).

Heptane/ethyl acetate at ratio 2 contains a greater proportion of ethyl acetate than heptane/ethyl acetate at ratio 1. Heptane/ethyl acetate at ratio 2 contains less than about 6% ethyl acetate, and heptane/ethyl acetate at ratio 1 contains less than about 3% ethyl acetate. The terms lower, intermediate, and higher (or more highly) refer to the degree of unsaturation of the individual components.

The step time is 10 minutes. The temperature of the system is ambient in the reload, higher and intermediate adsorption, and lower desorption zones; 35° C. in the intermediate desorption zone, and 40° C. in the ethyl acetate stripping zone. The flow rates would be as follows:

| Feed: | 0.4–1.0 ml/min. | Ethyl acetate: | 1.0–4.0 ml/min. |
|---|---|---|---|
| Hept/EA ratio 1: | 2.0–3.0 ml/min. | Reload: | 0.5–4.0 ml/min. |
| Hept/EA ratio 2: | 1.0–3.0 ml/min. | | |

The use of different ratios of heptane and ethyl acetate and different temperatures through the system allows for the elution of a lower unsaturated enriched effluent (C18:1), an intermediate unsaturated enriched effluent (C18:2); leaving primarily highly unsaturated methyl esters adsorbed on the adsorbent. The ethyl acetate elution, in the ethyl acetate stripping zone, causes the highly unsaturated methyl esters to desorb and the effluent from the column will therefore be enriched in highly unsaturated methyl esters (C18:3).

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated herein by reference.

Having now fully described this invention, it will be understood to those of ordinary skill in the art that the same can be performed within a wide and equivalent range of conditions, formulations, and other parameters without affecting the scope of the invention or any embodiment thereof.

What is claimed is:

1. A method of preparing an enriched composition, wherein said method is a simulated moving bed chromatographic process comprising:
  (a) combining a first composition comprising:
    i. at least one fatty acid ($C_{1-5}$) alkyl ester containing at least one saturated $C_{12-24}$ carbon chain and ii. at least one fatty acid ($C_{1-5}$) alkyl ester containing at least one unsaturated $C_{12-24}$ carbon chain with an argentized alumina having been conditioned by contacting with a non-polar solvent for at least about 24 hours in the absence of said first composition;

wherein said conditioned argentized alumina has a Hunter L color value that is at least about 20% lower than the Hunter L color value of said alumina prior to conditioning; and, wherein said conditioned argentized alumina is contained on chromatographic beds, columns or parts thereof arranged in a simulated moving bed chromatographic array;

(b) contacting said combined first composition and said conditioned argentized alumina with one or more solvents simultaneously or in sequence; and (c) eluting a second composition that is enriched relative to said first composition in at least one of said fatty acid (C1-5) alkyl esters containing at least one unsaturated $C_{12-24}$ carbon chain;

wherein a second composition enriched in one or more of said fatty acid (C1-5) alkyl esters containing an unsaturated $C_{12-24}$ carbon chain is prepared.

2. The method of claim 1, wherein said second composition comprises at least one fatty acid (C1-5) alkyl ester containing at least one monounsaturated $C_{12-24}$ carbon chain, and optionally at least one fatty acid (C1-5) alkyl ester containing at least one polyunsaturated $C_{12-24}$ carbon chain.

3. The method of claim 2, further comprising:
(d) combining said second composition with an adsorbent comprising said conditioned argentized alumina;
wherein said adsorbent is contained on chromatographic beds, columns or parts thereof arranged in a simulated moving bed chromatographic array;
(e) contacting said combined second composition and said adsorbent with one or more solvents simultaneously or in sequence; and
(f) eluting a third composition that is enriched relative to said second composition in said at least one fatty acid (C1-5) alkyl ester containing at least one monounsaturated $C_{12-24}$ carbon chain;
wherein a composition enriched in said at least one fatty acid (C1-5) alkyl ester containing at least one monounsaturated $C_{12-24}$ carbon chain is prepared.

4. The method of claim 3, further comprising:
(g) eluting a fourth composition that is enriched relative to said second composition in said at least one fatty acid (C1-5) alkyl ester containing at least one polyunsaturated $C_{12-24}$ carbon chain.

5. The method of claim 4, wherein said polyunsaturated $C_{12-24}$ carbon chain is di-unsaturated or tri-unsaturated.

6. The method of claim 4, further comprising:
subsequent to said step (f) and prior to said step (g), contacting said conditioned argentized alumina with one or more solvents simultaneously or in sequence.

7. The method of claim 4, further comprising:
(h) combining said fourth composition with an adsorbent comprising a conditioned argentized alumina;
wherein said conditioned argentized alumina is contained on chromatographic beds, columns or parts thereof arranged in a simulated moving bed chromatographic array;
(i) contacting said combined fourth composition and said third adsorbent with one or more solvents simultaneously or in sequence; and
(j) eluting a fifth composition that is enriched relative to said fourth composition in said at least one fatty acid (C1-5) alkyl ester containing at least one di-unsaturated $C_{12-24}$ carbon chain;
wherein a composition enriched in said at least one fatty acid (C1-5) alkyl ester containing at least one di-unsaturated $C_{12-24}$ carbon chain is prepared.

8. The method of claim 1, further comprising:
subsequent to said step (b) and prior to said step (c), eluting a composition enriched in at least one fatty acid (C1-5) alkyl ester containing at least one saturated $C_{12-24}$ carbon chain.

9. The method of claim 1, wherein said conditioned argentized alumina is selected from the group consisting of a conditioned spherical argentized alumina, a conditioned argentized neutral alumina, and a conditioned argentized acidic alumina, and combinations of any thereof.

10. The method of claim 1, wherein said simulated moving bed chromatographic process comprises one or more zones, wherein each zone is defined by the primary function of the one or more chromatographic bed(s), column(s) or parts thereof contained in each zone.

11. The method of claim 10, comprising the following zones:
(a) solvent A elution zone;
(b) solvent B elution zone;
(c) enrichment zone; and
(d) adsorption zone;
wherein said solvent A of (a) and solvent B of (b) are different.

12. The method of claim 11, wherein said solvent A is isopropanol and said solvent B is methanol.

13. The method of claim 11, wherein said solvent A is ethyl acetate and said solvent B is heptane.

14. The method of claim 10, comprising the following zones:
(a) higher and intermediate adsorption zone,
(b) lower desorption zone;
(c) intermediate desorption zone:
(d) stripping zone; and
(e) reload zone;
wherein a composition enriched in monounsaturated fatty acid methyl esters is passed out of the simulated moving bed as an effluent from the lower adsorption zone;
a composition enriched in C18:2 fatty acid methyl esters is passed out of the simulated moving bed as an effluent from the intermediate desorption zone; and
a composition enriched in C18:3 fatty acid methyl esters is allowed to pass out of the simulated moving bed as an effluent from the stripping zone.

15. The method of claim 14, wherein heptane/ethyl acetate at a ratio 1 is applied in the lower adsorption zone;
heptane/ethyl acetate at a ratio 2 is applied in the intermediate desorption zone; and
ethyl acetate is applied in the stripping zone;
wherein the content of ethyl acetate in heptane/ethyl acetate at ratio 1 is less than the content of ethyl acetate in heptane/ethyl acetate ratio 2.

16. A method of preparing an enriched composition, wherein said method is a simulated moving bed chromatographic process comprising:

(a) combining a first composition comprising:
  i. at least one fatty acid (C1-5) alkyl ester containing at least one saturated $C_{12-24}$ carbon chain and
  ii. at least one fatty acid (C1-5) alkyl ester containing at least one unsaturated $C_{12-24}$ carbon chain with an argentized alumina having been conditioned by contacting with a non-polar solvent for 48 hours in the absence of said first composition;
wherein said conditioned argentized alumina has a Hunter L color value that is at least about 20% lower than the Hunter L color value of said alumina prior to conditioning; and,
wherein said argentized conditioned alumina is contained on chromatographic beds, columns or parts thereof arranged in a simulated moving bed chromatographic array;
(b) contacting said combined first composition and said argentized conditioned alumina with one or more solvent(s) simultaneously or in sequence; and
(c) eluting a second composition that is enriched relative to said first composition in said at least one fatty acid (C1-5) alkyl ester containing at least one unsaturated $C_{12-24}$ carbon chain;
wherein a second composition enriched in said at least one fatty acid (C1-5) alkyl ester containing an unsaturated $C_{12-24}$ carbon chain is prepared.

17. A method of preparing an enriched composition, wherein said method is a simulated moving bed chromatographic process comprising:

(a) combining a first composition comprising:
  i. at least one fatty acid (C1-5) alkyl ester containing at least one monounsaturated $C_{12-24}$ carbon chain and
  ii. at least one fatty acid (C1-5) alkyl ester containing at least one polyunsaturated $C_{12-24}$ carbon chain
with an argentized alumina having been conditioned by contacting with a non-polar solvent for 72 hours in the absence of said first composition;
wherein said conditioned argentized alumina has a Hunter L color value that is at least about 20% lower than the Hunter L color value of said alumina prior to conditioning; and,
wherein said conditioned argentized alumina is contained on chromatographic beds, columns or parts thereof arranged in a simulated moving bed chromatographic array;
(b) contacting said combined first composition and said conditioned argentized alumina with one or more solvent(s) simultaneously or in sequence; and
(c) eluting a second composition that is enriched relative to said first composition in said at least one fatty acid (C1-5) alkyl ester containing at least one polyunsaturated $C_{12-24}$ carbon chain;
wherein a second composition enriched in said at least one fatty acid (C1-5) alkyl ester containing a polyunsaturated $C_{12-24}$ carbon chain is prepared.

18. The method of claim 1, wherein said fatty acid (C1-5) alkyl esters are ethyl esters or methyl esters.

* * * * *

UNITED STATES PATENT AND TRADEMARK OFFICE
CERTIFICATE OF CORRECTION

PATENT NO. : 7,667,061 B2  Page 1 of 1
APPLICATION NO. : 11/612250
DATED : February 23, 2010
INVENTOR(S) : Binder et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 441 days.

Signed and Sealed this

Seventh Day of December, 2010

David J. Kappos
*Director of the United States Patent and Trademark Office*